United States Patent
Martin et al.

(10) Patent No.: US 10,258,620 B2
(45) Date of Patent: Apr. 16, 2019

(54) CRYSTALLINE FORM OF 5-AMINO-2,3-DIHYDROPHTHALAZINE-1,4-DIONE SODIUM SALT, PHARMACEUTICAL PREPARATIONS CONTAINING THE SAME AND METHOD FOR THE PRODUCTION OF SAID FORM

(71) Applicant: METRIOPHARM AG, Zürich (CH)

(72) Inventors: Thomas Martin, Selb (DE); Josef Breu, Bayreuth (DE); Wolfgang Brysch, Berlin (DE); David Kosel, Leipzig (DE); Beate Ludescher, Berlin (DE); Michael Niedermaier, Berlin (DE); Jörg Von Wegerer, Berlin (DE)

(73) Assignee: Metriopharm AG, Zürich (CH)

( * ) Notice: Subject to any disclaimer, the term of this patent is extended or adjusted under 35 U.S.C. 154(b) by 0 days.

(21) Appl. No.: 15/536,634

(22) PCT Filed: Dec. 18, 2015

(86) PCT No.: PCT/EP2015/002555
§ 371 (c)(1),
(2) Date: Jun. 16, 2017

(87) PCT Pub. No.: WO2016/096143
PCT Pub. Date: Jun. 23, 2016

(65) Prior Publication Data
US 2017/0368063 A1 Dec. 28, 2017

(30) Foreign Application Priority Data
Dec. 18, 2014 (EP) ..................................... 14004274

(51) Int. Cl.
*C07D 237/32* (2006.01)
*A61K 31/502* (2006.01)

(52) U.S. Cl.
CPC .......... *A61K 31/502* (2013.01); *C07D 237/32* (2013.01)

(58) Field of Classification Search
CPC ................................................... C07D 237/32
See application file for complete search history.

(56) References Cited

U.S. PATENT DOCUMENTS 8,536,171 B2 * 9/2013 Abidov ............... A61K 31/502
514/248

FOREIGN PATENT DOCUMENTS

EP 1 203 587 A1 5/2002
WO WO 2011/107295 A1 9/2011

OTHER PUBLICATIONS

V. B. Rybakov et al., "On the structure of luminol sodium salts," Crystallography Reports, vol. 59, No. 3, May 1, 2014 (May 1, 2014), pp. 383-393, XP055256453.
Haleblian J. et al., "Pharmaceutical Applications of Polymorphism," Journal of Pharmaceutical Sciences, American Pharmaceutical Association, Washington, US, vol. 58, No. 8, Aug. 1, 1969 (Aug. 1, 1969), pp. 911-929, XP009058367.
International Search Report and Written Opinion dated Mar. 18, 2016 in corresponding International Application No. PCT/EP2015/002555.

* cited by examiner

*Primary Examiner* — Brian E McDowell
(74) *Attorney, Agent, or Firm* — Haug Partners LLP

(57) ABSTRACT

The invention relates to the provision of a new crystalline form for 5-amino-2,3-dihydrophthalazine-1,4-dione sodium, the use of this form for medical purposes, methods for producing the crystalline form according to the invention, as well as pharmaceutical preparations comprising said form.

2 Claims, 24 Drawing Sheets

Form I

Form II

Form III

Form I

Form II

Form III

Form I

Form II

Form III

Form I

Form II

Form III

Form I

Form II

Form III

Form I

Form II

Form III

Form I

Form II

Form III

Form II

Form III

Form II

Form III

Form II

Form III

Form II

Form III

CRYSTALLINE FORM OF 5-AMINO-2,3-DIHYDROPHTHALAZINE-1,4-DIONE SODIUM SALT, PHARMACEUTICAL PREPARATIONS CONTAINING THE SAME AND METHOD FOR THE PRODUCTION OF SAID FORM

CROSS-REFERENCE TO RELATED APPLICATIONS

This application is the National Stage entry under 35 U.S.C. § 371 of International Application No. PCT/EP2015/002555 filed on Dec. 18, 2015, published on Jun. 23, 2016 under Publication Number WO 2016/096143, which claims the benefit of priority under 35 U.S.C. § 119 of European Patent Application Number 14004274.8 filed Dec. 18, 2014.

TECHNICAL FIELD OF THE INVENTION

The present invention relates to the provision of a new crystalline form of 5-amino-2,3-dihydrophthalazine-1,4-dione sodium salt with advantageous properties, pharmaceutical preparations containing the same, and methods for producing the same.

The invention in particular relates to the provision of a new crystalline form of 5-amino-2,3-dihydrophthalazine-1,4-dione sodium salt for medical purposes.

BACKGROUND OF THE INVENTION

For quite some time chemical compounds having immunomodulatory effects are known in the art. To these compounds also belongs 5-amino-2,3-dihydrophthalazine-1,4-dione sodium salt. This compound is known from EP 1 203 587 A and has the following basic structure (Na$^+$ not shown):

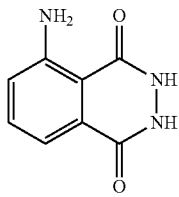 [SMILES: Nc1cccc2c(=O)[nH][nH]c(=O)c12]

The above basic structure is also called luminol. Other common synonymous terms are 3-aminophthalhydrazide, 3-aminophthalic hydrazide, o-aminophthalhydrazide and o-aminophthalic hydrazide. It is known from prior art that 5-amino-2,3-dihydrophthalazine-1,4-dione alkali salts crystallize as solids in different hydrate forms. In prior art, in particular the dihydrate of the sodium salt (RU2113222C1) and a trihydrate of the potassium salt and mixed forms thereof (RU2211036C2) are described. In addition, crystal structures of 5-amino-2,3-dihydrophthalazine-1,4-dione alkali salts partially differing in their hydration stage are known from scientific literature. A structural characterization is provided for a potassium salt anhydrate, a lithium salt monohydrate, a rubidium salt dihydrate, a caesium salt trihydrate and a sodium salt hexahydrate (cf. Guzei et al. (2013): Journal of Coordination Chemistry, 66:21, 3722-3739). Also a dihydrate as well as two polymorphic anhydrates of the sodium salt have been characterized structurally. The characterization was conducted from mixtures containing either both of said anhydrate forms or all three forms (cf. Rybakov et al. (2014): Crystallography Reports, 59, 383-393).

Pure crystalline forms of 5-amino-2,3-dihydrophthalazine-1,4-dione sodium salt anhydrate were first described in WO2011/107295A1 as form I and form II. The crystalline forms disclosed in WO2011/107295A1 were characterized by a X-ray powder diffractogram, expressed in D or 2-theta values, whereas "D" represents interplanar spacings and "2-theta" represents the 2-theta angles in degrees. The interplanar spacing D (also d) describes the vertical distance between two consecutive lattice planes. The Bragg angle theta (θ) indicates the characteristic angle resulting of the reflection of the incident X-ray beam at a lattice layer of the crystal, thereby producing a X-ray diffraction pattern. Both parameters are linked via the Bragg formula:

$$n\lambda = 2d\sin(\theta).$$

By these characteristic values d and θ a crystal is characterized necessarily and sufficiently.

D-values were disclosed in WO2011/107295A1 with 13.5; 6.9; 5.2; 4.6; 3.9; 3.5; 3.4; 3.3; 3.1 and 3.0 for form I; and with 12.9; 7.9; 7.1; 6.5; 5.3; 4.0; 3.7; 3.6; 3.3 and 3.2 for form II. 2-theta-angles were disclosed with 6.5; 12.7; 16.9; 19.3; 22.8; 25.8; 26.6; 27.2; 28.7 and 30.3 for form I; and with 6.8; 11.2; 12.5; 13.7; 16.7; 22.4; 24.3; 24.9; 27.2 and 27.8 for form II.

In addition, the relative intensities of the reflections were reported.

WO2011/107295A1 also lists a number of rather complex methods of production for both form I as well as form II.

It is known in the art that crystalline forms of a substance can differ in their physical properties such as solubility, dissolution rate, and stability (cf. Haleblian und McCrone (1969): Journal of Pharmaceutical Sciences, 58:911-929). Such properties can affect the pharmaceutical processing of the active ingredient as well as its biological availability and pharmacokinetics, and thus its biological efficacy (cf. Griesser (2006) in: Polymorphisms in the Pharmaceutical Industry. Hilfiker (Ed.) 211-234). For the production of medicines it is important that the starting material is stable, not hygroscopic and controllable in its behavior as a solid during the complete production process. Further, the chemical stability and solid-phase stability (phase purity) with long storability of an active ingredient is extremely important (cf. Miller et al. (2006) in: Polymorphisms in the Pharmaceutical Industry. Hilfiker (Ed.) 385-403). It is desirable that even over a longest possible storing time the physical properties of the active ingredient will be maintained. This relates e.g. to the hygroscopicity, solubility or initial dissolution rate of the active ingredient, but also to phase purity.

Very important for the pharmaceutical processing and the medical use are production methods which reliably and reproducibly permit the production of the desired crystalline forms. When producing crystalline forms, it should be considered that even small deviations of the process parameters will cause changes of the crystal structure of the products and can thus finally lead to different crystalline forms or mixed forms. Properties changed thereby—for instance a modified biological efficacy by a different solubility—may lead to a rejection of complete batches. Often it is not possible at all to produce the desired form (cf. Ulrich und Jones (2005): Nachrichten aus der Chemie 53:19-23). Besides phase purity of the active ingredient and the resulting possible changes in the efficacy further important properties for the pharmaceutical processing can be affected in an adverse manner, e.g. the capability to be pressed to tablets by an impairment of the pourability or of the flow rate of the crystalline form.

5-amino-2,3-dihydrophthalazine-1,4-dione alkali salts belong to the group of aminophthalhydrazides and are described in prior art as immunomodulators with specific anti-inflammatory, antioxidative and antitoxic properties (cf. WO2011/107295A1, U.S. Pat. No. 6,489,326B1; EP0617024B1, U.S. Pat. No. 5,512,573A, U.S. Pat. No. 5,543,410A, U.S. Pat. No. 7,326,690B2).

Immunomodulatory substances are commonly classified according to their effects into immunosuppressants and immunostimulants (cf. Rote Liste Service GmbH (2014): www.rote-liste.de, access on Sep. 2, 2014). The corresponding preparations with an exclusively immunosuppressive or an exclusively immunostimulatory effect, such as immunosuppressive TNF alpha blockers or immunostimulatory interferon beta preparations, often cause significant undesired side effects in the organism, actually because of their very specific mode of action. Some known immunosuppressive substances, such as the TNF alpha blocker adalimumab, specifically inhibit certain inflammatory mediators. Such therapies are known to have serious side effects (cf. Descotes (2008): Expert Opin. Drug Metab. Toxicol., 4:12: 1537-1549), since the blocking of individual inflammatory mediators is a severe intervention into the complex immune system. For instance, in the case of adalimumab opportunistic infections such as sepsis occur frequently, occasionally malign lymphoma can occur as well. Consequently the organism is not capable anymore to fulfil its functions, hence reacting automatically and physiologically in an appropriate manner to exogenous and endogenous inflammatory stimuli such as bacterial infections. Thus, for instance, the application of TNF alpha blockers is contraindicated in the case of serious infections, this applies in particular for sepsis and tuberculosis. Before administering a corresponding medication, e.g. for the treatment of rheumatoid arthritis, a TBC screening is strongly recommended. Moreover, Hoffmann (2005: Intensivmed 42:371-377) could clearly demonstrate that TNF alpha blockers are not suitable for the clinical application in case of septic conditions, but to the contrary may even lead to an increased mortality.

The particular pharmacologic properties of the 5-amino-2,3-dihydrophthalazine-1,4-dione alkali salts are, however, very useful, a.o. for the prevention of so-called cytokine storms caused by excessive immune responses. In contrast to the so-called cytokine blockers these salts are mostly free of side effects since an inhibition of individual cytokines will not take place, but these are regulated to a physiological level, and thus an adequate reaction of the organism to infectious pathogens is assured further on. Correctly speaking, the term to use in this case should be immunoregulators instead of immunomodulators.

SUMMARY OF THE INVENTION

In the manufacture of medicinal products, in particular concerning the dosing of active ingredients in pharmaceutical preparations, the bulk density as a substance property plays a major role. In particular too low bulk densities can cause problems in the production process, ranging from poor flow properties to difficulties in the exact dosing. Another common problem with medicinal products, particularly in case of polymorphic agents, is to maintain phase purity of the active ingredient over a longer period of time (shelf life). In particular in pharmaceutical preparations which include the risk of wetting of the active substance with solvents, as it may be the case e.g. in tablets, creams, lotions or emulsions, the risk of a solid phase transition is particularly high, especially within the shelf life that for economic reasons is as long as possible.

Task of the present invention was to provide a new anhydrate form of 5-amino-2,3-dihydrophthalazine-1,4-dione sodium salt having advantageous characteristics, in particular an improved storage ability and/or an improved bulk density, that thus can be used specifically for medical, particularly anti-inflammatory and immunoregulatory purposes. Furthermore, the provided form shall have physicochemical properties, which are advantageous for medicinal products manufactured, stored and/or applied therewith, individually or in combination.

The task was solved by the provision of a novel anhydrate form for 5-amino-2,3-dihydrophthalazine-1,4-dione sodium salt (form III), which, based on experimental data of physicochemical and biological characteristics, surprisingly and verifiably contrasts with prior art and in particular contrasts with anhydrate forms I and II of 5-amino-2,3-dihydrophthalazine-1,4-dione sodium salt as disclosed in WO2011/107295A1.

The crystalline anhydrate form III (form III) is defined by 15 characteristic values each of interplanar spacings and 2-theta angles (see Table 1) expressed in a X-ray powder diffractogram (FIG. 1). Form III is further defined by a structure solution and Rietveld refinement from XRPD data using the TOPAS Academic software (Tab. 2) resulting in the crystalline structure with the respective packing motifs (FIG. 2), as well as by a solid state-FT-IR spectrum (FIG. 3) and a Raman spectrum (FIG. 4).

Differences concerning physical characteristics between the form according to the invention and the pure anhydrate forms of 5-amino-2,3-dihydrophthalazine-1,4-dione sodium salt as disclosed in prior art exist for example in bulk density and storage ability. Compared to form I and II the form III according to the invention is characterized by both an improved bulk density and also an improved storage ability, wherein the bulk density of individual batches of form III according to the invention is higher than 150 kg/m$^3$, preferably higher than 175 kg/m$^3$, mostly preferred higher than 200 kg/m$^3$, and wherein the storage ability refers in particular to the maintenance of phase purity, preferably in situations where wetting—intentionally or unintentionally—may happen, wherein already low amounts of solvent can cause a partial phase transition.

Further, the inventors have set themselves the task to provide one or more methods for producing the novel anhydrate form of 5-amino-2,3-dihydrophthalazine-1,4-dione sodium salt according to the invention in a feasible, economical and reproducible way.

The illustrated methods shall preferably be carried out without the use of heavy metal catalysts and shall permit the reproducible production of the novel crystalline form III also for any desired batch size.

This task was solved by the methods according to the invention for producing crystalline form III. In one method according to the invention initially any form for 5-amino-2,3-dihydrophthalazine-1,4-dione sodium salt anhydrate is produced and afterwards completely dissolved in DMSO (dimethyl sulfoxide) while stirring. DMSO is evaporated until a suspension occurs, the suspension is then dried up. This method according to the invention can be used for any desired batch size. The 5-amino-2,3-dihydrophthalazine-1, 4-dione sodium salt used as starting material for the production should be as pure as possible. It can be produced, for example, by reduction of 3-nitrophthalic acid in alkaline medium using a suitable reducing agent via 3-nitrophthalanhydride. Optional purification steps by recrystallization may follow. Furthermore, a particularly advantageous method for producing anhydrate form II for 5-amino-2,3-dihydrophthalazine-1,4-dione sodium salt anhydrate is presented.

The present invention finally comprises the use of form III for medical purposes as a single agent or in combination with one or more other active ingredients, as well as pharmaceutical preparations containing form III alone or in combination with one or more other active ingredients.

SHORT DESCRIPTION OF THE FIGURES

FIG. 1 describes a powder diffractogram of crystalline form III according to the invention, wherein FIG. 1a displays the plot of the Rietveld refinement over the full recorded range from 3-80.085 °2θ, whereas FIG. 1b displays a section of the plot within the range of 3-35 °2θ.

FIG. 2 displays a comparative presentation of the packing motifs in the crystal structures of forms I and II as well as of form III according to the invention in the respective direction of the unit cell axes, illustrated as ball-and-stick model and as calotte model.

FIG. 2a shows the a-axis in the ball-and-stick model,
FIG. 2b shows the a-axis in the calotte model,
FIG. 2c shows the b-axis in the ball-and-stick model,
FIG. 2d shows the b-axis in the calotte model,
FIG. 2e shows the c-axis in the ball-and-stick model,
FIG. 2f shows the a-axis in the calotte model.

FIG. 3 displays a solid state FT-IR spectrum of form III according to the invention, wherein FIG. 3a displays the plot over the full recorded range from 4000-400 cm$^{-1}$, whereas FIG. 3b displays a section of the plot within the range of 1800-400 cm$^{-1}$.

FIG. 4 displays a Raman spectrum of form III within the range of 90-1800 cm$^{-1}$.

FIG. 5 displays SEM recordings of forms I and II, as well as of form III according to the invention.

Figure 6A:
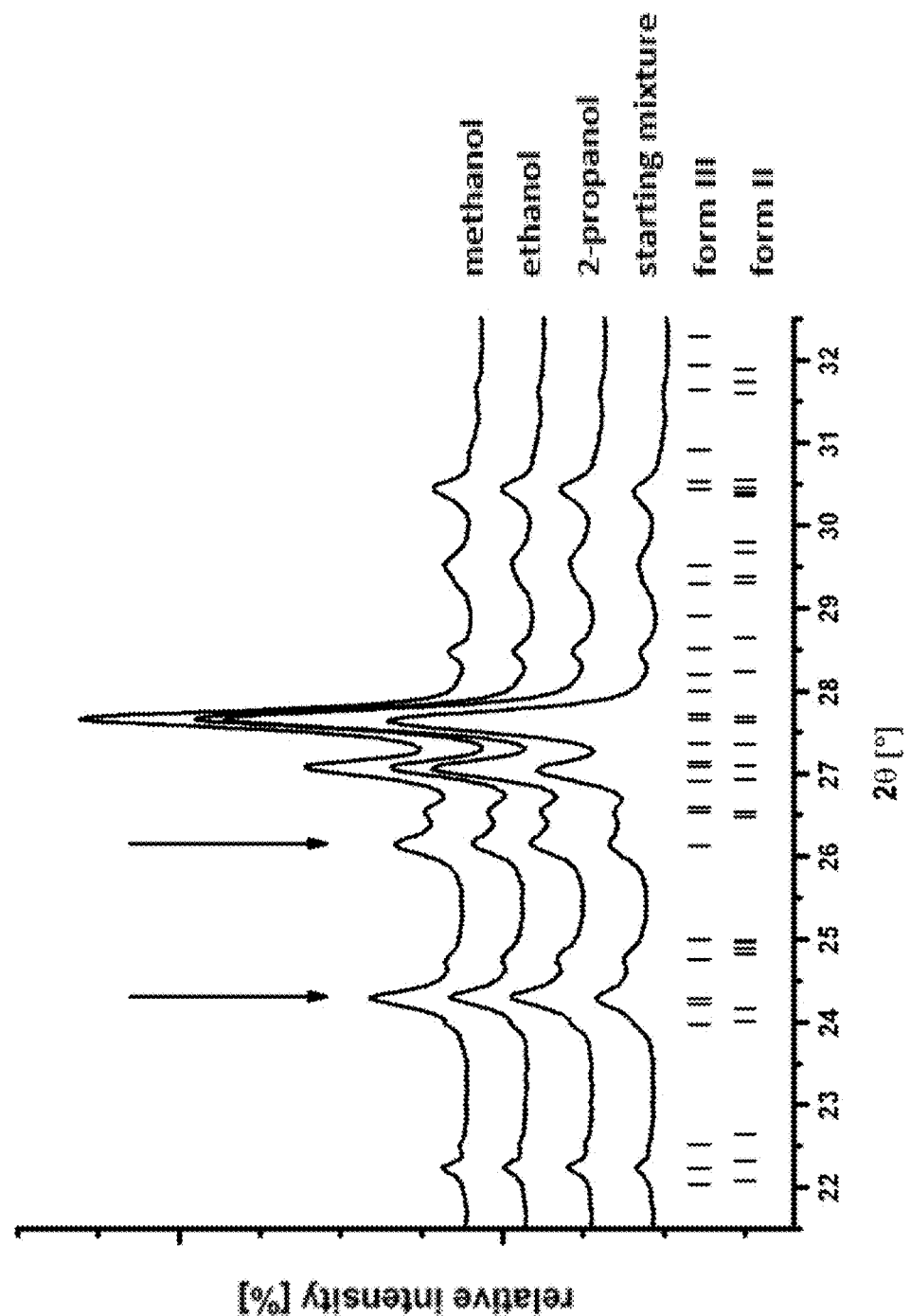
Figure 6B:
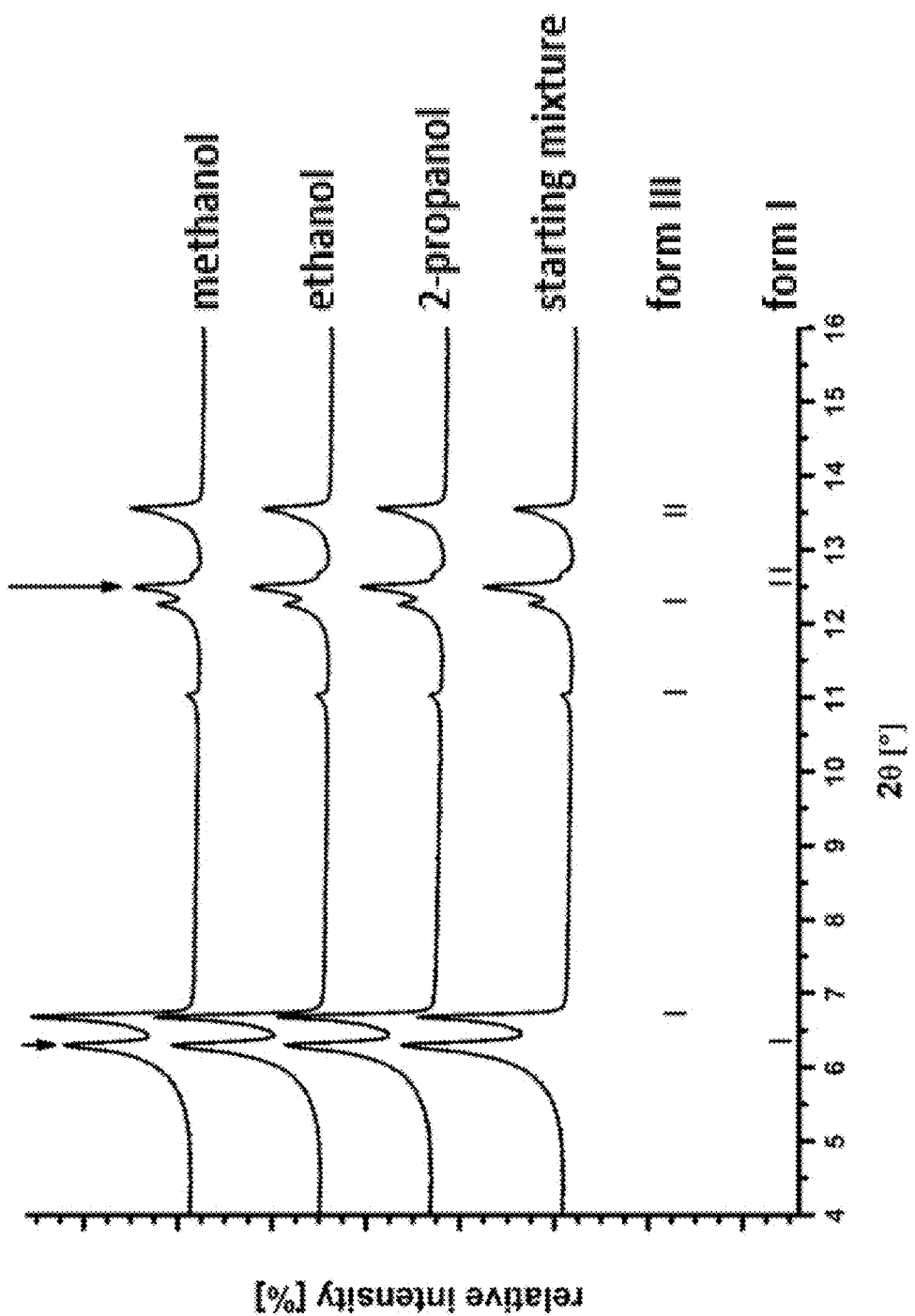

FIG. 6: Powder diffractograms of suspensions of a 50:50 wt % mixture of forms II and III in 2-propanol, ethanol and methanol after equilibration for 24 h (FIG. 6a), respectively of a 50:50 wt % mixture of forms I and III in 2-propanol, ethanol and methanol after equilibration for 3 days (FIG. 6b). For comparison a diffractogram of the respective starting mixtures is shown as well.

In FIG. 6a singular reflexes for form III with increasing intensities are highlighted by arrows. (I) show the reflection positions of the respective form.

In FIG. 6b singular reflexes for form I with decreasing intensities are highlighted by arrows. (I) show the reflection positions of the respective form.

FIG. 7 displays the secretion of the cytokines TNF alpha and IL-6 of differentiated HL60 cells in pg/mL after respective pre-stimulation for 1 h with 5-amino-2,3-dihydrophthalazine-1,4-dione sodium salt dihydrate, the anhydrate forms I, II and III or a negative control and subsequent stimulation with 100 ng/mL lipopolysaccharides (LPS) for 24 h (mean is based on 3 measurements, respectively).

Figure 7A:
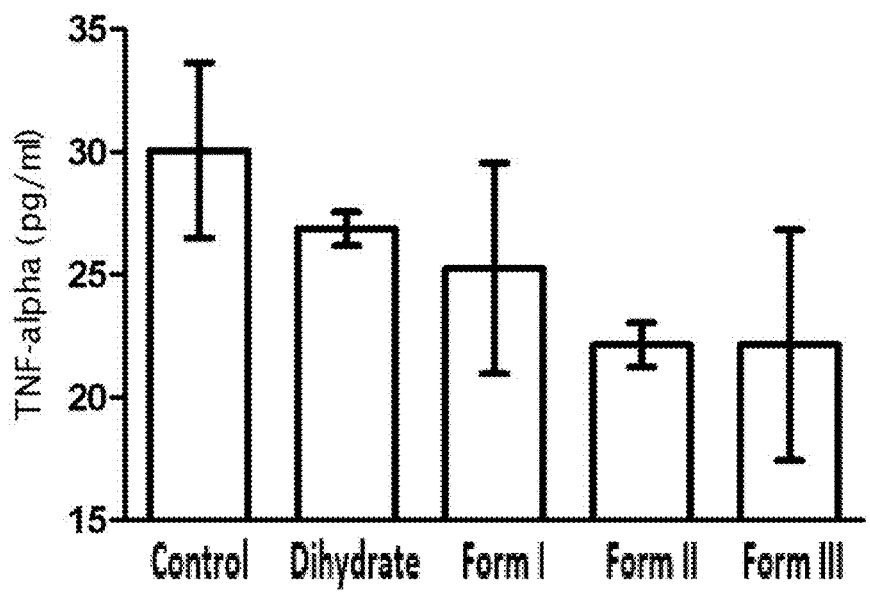

FIG. 7a shows the TNF alpha secretion of differentiated HL60 cells in pg/mL and

Figure 7B:
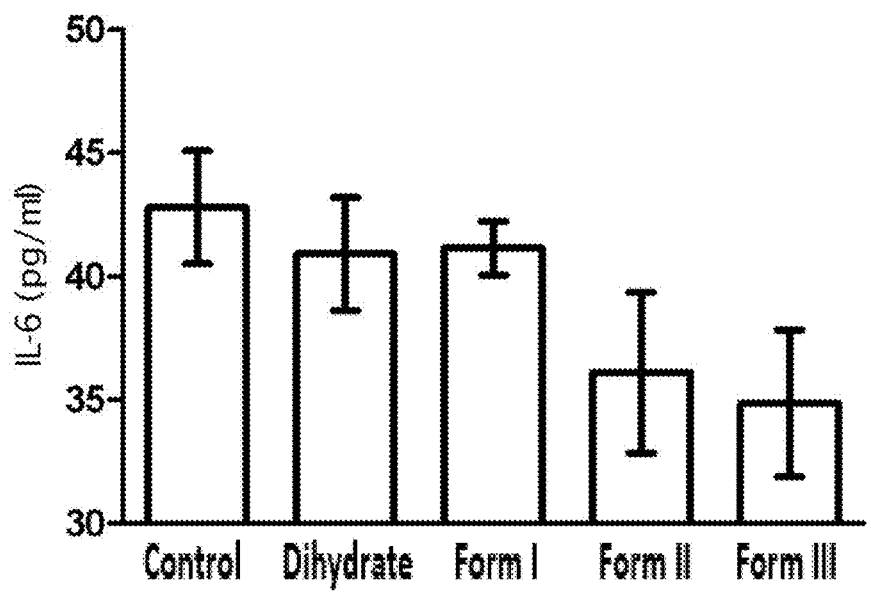

FIG. 7b shows the IL-6 secretion of differentiated HL60 cells in pg/mL.

Figure 8:
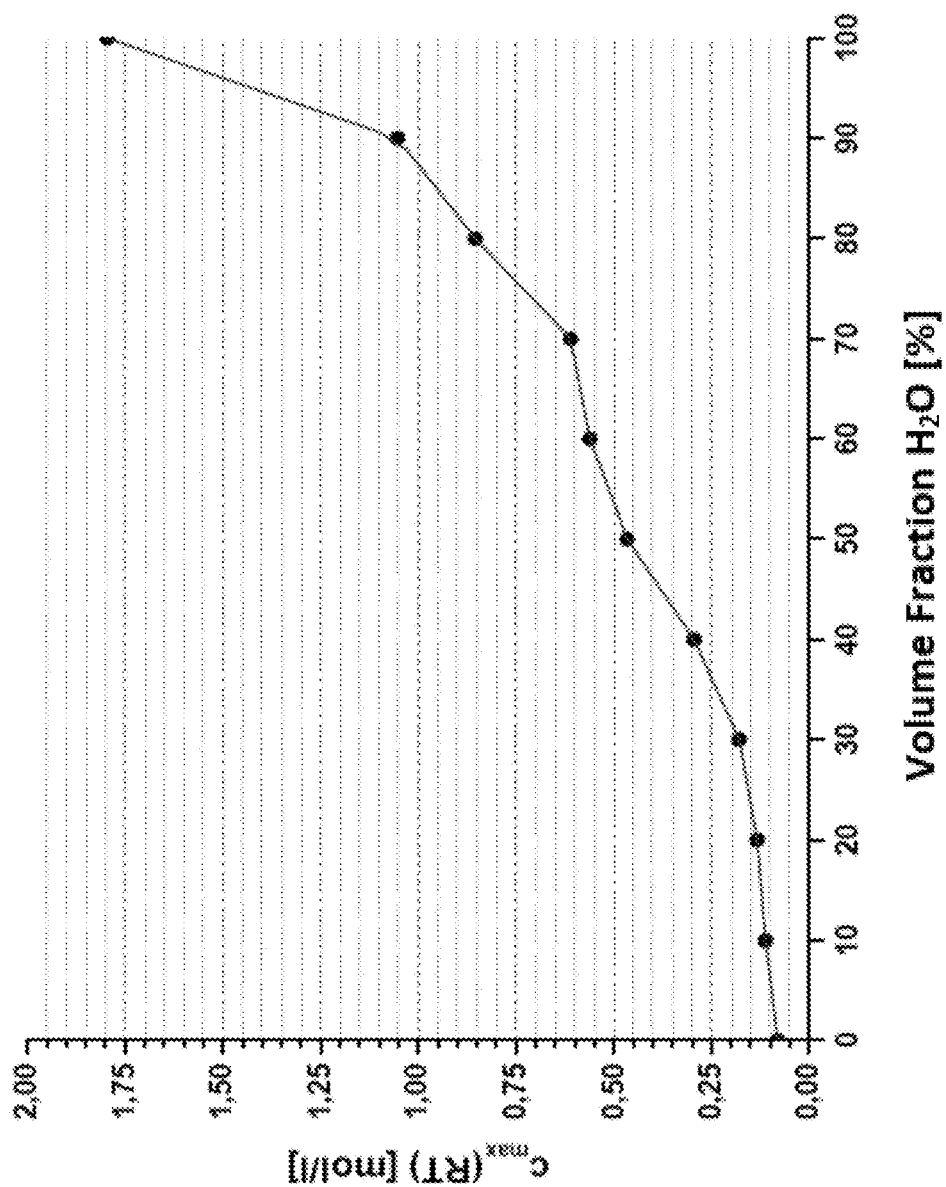

FIG. 8 displays the solubility of 5-amino-2,3-dihydrophthalazine-1,4-dione sodium salt in mol/l in a DMSO-$H_2O$ mixture with an increasing proportion of $H_2O$. With an increasing proportion of $H_2O$ the solubility increases continuously.

DETAILED DESCRIPTION

Unless otherwise shown, the technical and scientific terms used in the present invention have the meaning that a person skilled in the relevant technical art will attribute to them.

Definitions

"Form I" and "form II" are crystalline forms of 5-amino-2,3-dihydrophthalazine-1,4-dione sodium salt known from WO2011/107295A1. To enhance readability these terms will be maintained.

"Form II" is a crystalline form of 5-amino-2,3-dihydrophthalazine-1,4-dione sodium salt according to the invention.

The terms "medicine" and "for use in medicine" refer to both human medicine and veterinary medicine.

The term "active ingredient" in a broader sense comprises each pharmacologically active component of a medical product. An active ingredient can be applied alone—as a single agent—or in a pharmaceutical preparation.

An "organism" in the scope of the present invention is a form of animal life, in particular human, pet or livestock.

The term "pharmaceutical preparation" or "pharmaceutical composition" comprises the active ingredient according to the invention in any pharmacologically suitable defined dose and dosage form and at least one pharmaceutically acceptable excipient. The term can also comprise further active ingredients alone or in combination.

The term "excipient" is used herein to describe any component of a pharmaceutical preparation besides the active ingredient itself. The choice of a suitable excipient depends on factors such as route of administration and dose as well as on the influence on solubility and stability of the preparation by the excipient itself. Pharmaceutical excipients are substances that are known to the person skilled in the art or can be obtained from standard pharmaceutical textbooks or official pharmacopeias (e.g. European pharmacopeia). Examples for excipients comprise: carriers, adjuvants, additives in general and especially fillers (basis), coatings, lubricants, glidants, releasing agents, flow regulators, humectants, rapid dissolution agents, disintegrants, sweeteners, aromas, flavor modifiers, flavors, preservatives, dispersants, coloring agents, solvents, solubilizers (wetting agents) and dissolution retardants, absorption enhancers and absorption retardants (retard preparations), penetration enhancers, diluents, gel forming agents, thickening agents, binders, absorbents, flavoring agents, aromatic substances, antioxidants, surfactants, emulsifiers, triglycerides, pH regulators (buffers), fatiquors, consistency enhancers, hydrotropes and substances producing gas when chemically reacting with water.

"Adjuvants" are excipients which (are able to) enhance the effect of the active ingredient such as solubilizers, surfactants, absorption enhancers and penetration enhancers.

The terms "buffer", "buffer system" and "buffer solution" refer to the ability of a system, in particular of an aqueous solution, to withstand a pH change due to the addition of an acid or a base or due to dilution with a solvent within the range provided by the respective buffering capacity.

The term "disintegrant" refers to materials which are added to a composition so that it can be broken apart more easily (e.g. tablets) or swells more easily.

The term "binder" refers to materials which are added to a composition for gluing together the single substances contained in the composition, in particular solids with a fine degree of dispersion or for gluing together with another composition, or with a base.

The term "lubricant" refers to substances which are added to the dosage form to facilitate the removal of tablets, granulates etc., e.g. from a mold or nozzle after pressing by reducing friction or abrasion.

"Glidants" are materials which prevent caking and improve the flow properties of the individual components of the composition, so that the flow is smooth and homogenous.

"Coloring agents" or "dyes" are auxiliary agents providing color to the composition or dosage form.

The term "free from phase shift" or "phase purity" means solid phase purity of a polymorphic active ingredient of at least 90%, preferred of at least 95%, particularly preferred of at least 98%, mostly preferred of at least 99%.

The term "effect" describes any intrinsic mode of action of an active ingredient.

The term "shelf life" or "storage ability" describes the stability, in particular the maintenance of phase purity, of an active ingredient as single substance and/or in a pharmaceutical preparation.

New Crystalline Form III of 5-amino-2,3-dihydrophthalazine-1,4-dione sodium salt The present invention includes a new crystalline anhydrate form (form III) of 5-amino-2,3-dihydrophthalazine-1,4-dione sodium salt characterized by an x-ray powder diffractogram of a Bragg-Brentano diffractometer (STOE STADI P) provided with a DECTRIS MythenIK detector using mono-chromatized (Ge111-monochromator) copper emissions Cu K($\alpha$1) (wave length $\lambda$=1,54187 Å) and expressed in D or 2-theta values (Table 1), whereas "D" represents interplanar spacings and "2-theta" represents the 2-theta angles in degrees. $I/I_o$ represents the relative intensities of the reflections, in Table 1 presented both in percent (%) and in a ordinal scale (rel).

TABLE 1

D values, 2-theta values and relative intensities $I/I_o$ for Form III

| D | 2-theta | $I/I_o$ (%) | $I/I_o$ (rel) |
|---|---|---|---|
| 13.131 | 6.73 | 100.00 | vst |
| 7.987 | 11.07 | 3.84 | vw |
| 7.186 | 12.31 | 10.06 | w |
| 6.566 | 13.48 | 5.07 | w |
| 6.512 | 13.59 | 25.59 | m |
| 5.372 | 16.49 | 11.21 | w |
| 3.994 | 22.24 | 2.43 | vw |
| 3.662 | 24.29 | 22.51 | m |
| 3.406 | 26.14 | 15.19 | m |
| 3.288 | 27.10 | 41.04 | w |
| 3.283 | 27.14 | 10.62 | w |
| 3.222 | 27.67 | 44.69 | st |
| 3.215 | 27.72 | 19.65 | m |

TABLE 1-continued

D values, 2-theta values and relative intensities $I/I_o$ for Form III

| D | 2-theta | $I/I_o$ (%) | $I/I_o$ (rel) |
|---|---|---|---|
| 3.127 | 28.52 | 3.20 | vw |
| 2.889 | 30.93 | 4.80 | w | given that:
vw = very weak (0% < $I/I_0$ ≤ 5%)
w = weak (5% < $I/I_0$ ≤ 15%)
m = medium (15% < $I/I_0$ ≤ 35%)
st = strong (35% < $I/I_0$ ≤ 75%)
vst = very strong (75% < $I/I_0$ ≤ 100%)

Anhydrate form III is further characterized by crystallographic data (cell parameters of the unit cell, crystal system, space group) (Table 2) as well as by the crystalline structure and the respective packing motifs, displayed as ball-and-stick model and as calotte model (FIG. 2). Whilst calotte models—due to the space-filling display of the atoms—create a three-dimensional rendition of the molecules and thus their orientation alongside the viewed direction in space (unit cell axes) becomes apparent, ball-and-stick models—due to the waiver of a space-filling display—allow a better in-depth view into the inner structure. The structure solution and Rietveld refinement has been conducted from XRPD data, recorded at a Bragg-Brentano diffractometer (STOE STADI P) provided with a DECTRIS MythenIK detector using mono-chromatized (Ge111-monochromator) copper emissions Cu K($\alpha$1) (wave length $\lambda$=1,54187 Å), using the software TOPAS Academic.

TABLE 2

Data on structure solution and Rietveld refinement of form III from XRPD data (numbers in brackets represent the standard deviations of the respective value):

| Chemical formula | | $C_8H_6N_3NaO_2$ |
|---|---|---|
| Molar mass [g/mol] | | 199.15 |
| Crystal system | | monoclinic |
| Space group | | P $2_1$/c |
| Axis lengths of the unit cell | a [Å] | 8.0364(2) |
| | b [Å] | 3.69765(5) |
| | c [Å] | 26.4246(7) |
| Angles between the axes of the unit cell | $\alpha$ [°] | 90 |
| | $\beta$ [°] | 96.346(2) |
| | $\gamma$ [°] | 90 |
| Volume of the unit cell | V [Å$^3$] | 780.416(33) |
| Number of formula units per unit cell/ Number of formula units per asymmetric unit | Z/Z' | 4/1 |
| Packing density (volume of all atoms in the cell/volume unit cell) | $\rho$ [g cm$^{-3}$] | 1.69491(7) |
| Structure factor of zeroth order (for h = k = l = 0). | F(000) | 408 |
| Measurement temperature [° C.] | | 295(2) |
| Data range [°2$\theta$] | | 3-80.085 |
| Reflections used | | 481 |
| Refined parameters | | 66 |
| Quality factors (residual values, R-factors) of the structure refinement: | $R_p$ | 0.0214 |
| | $R_{wp}$ | 0.0296 |
| | $R_{exp}$ | 0.0104 |
| | $R_{Bragg}$ | 0.0148 |

In case of X-ray experiments the non-dispersive structure factor F(000) specifies the number of electrons per unit cell. The quality factors $R_p$ and $R_{wp}$ refer to the goodness-of-fit between the calculated and the measured XRPD profile. $R_{exp}$ represents the lowest possible value of $R_{wp}$ that can be obtained when applying the theoretical structure model and the number of refined parameters. $R_{Bragg}$ refers to the accuracy of the refined structure model with regard to the extracted reflection intensities.

Figure 1A:
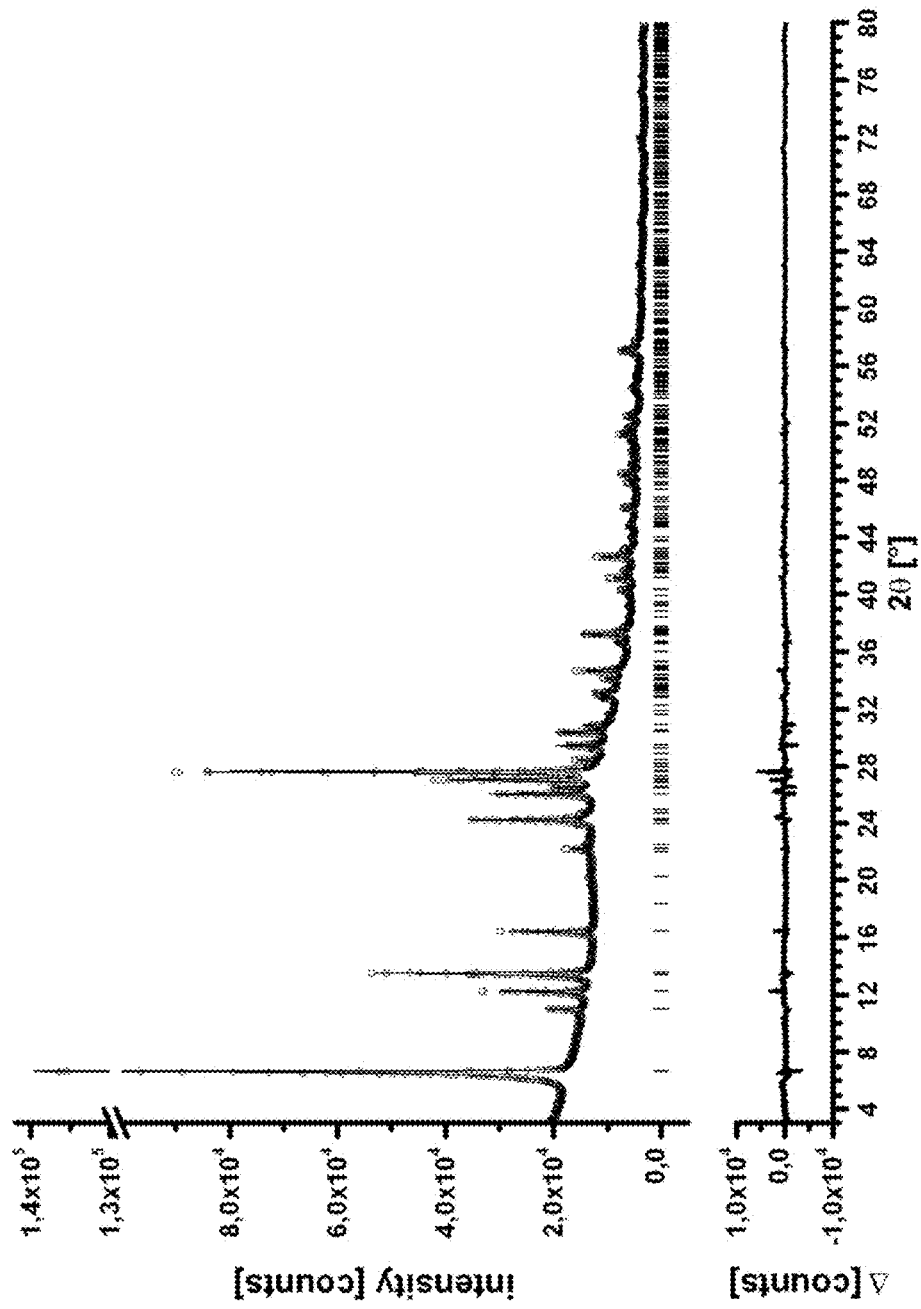
Figure 1B:
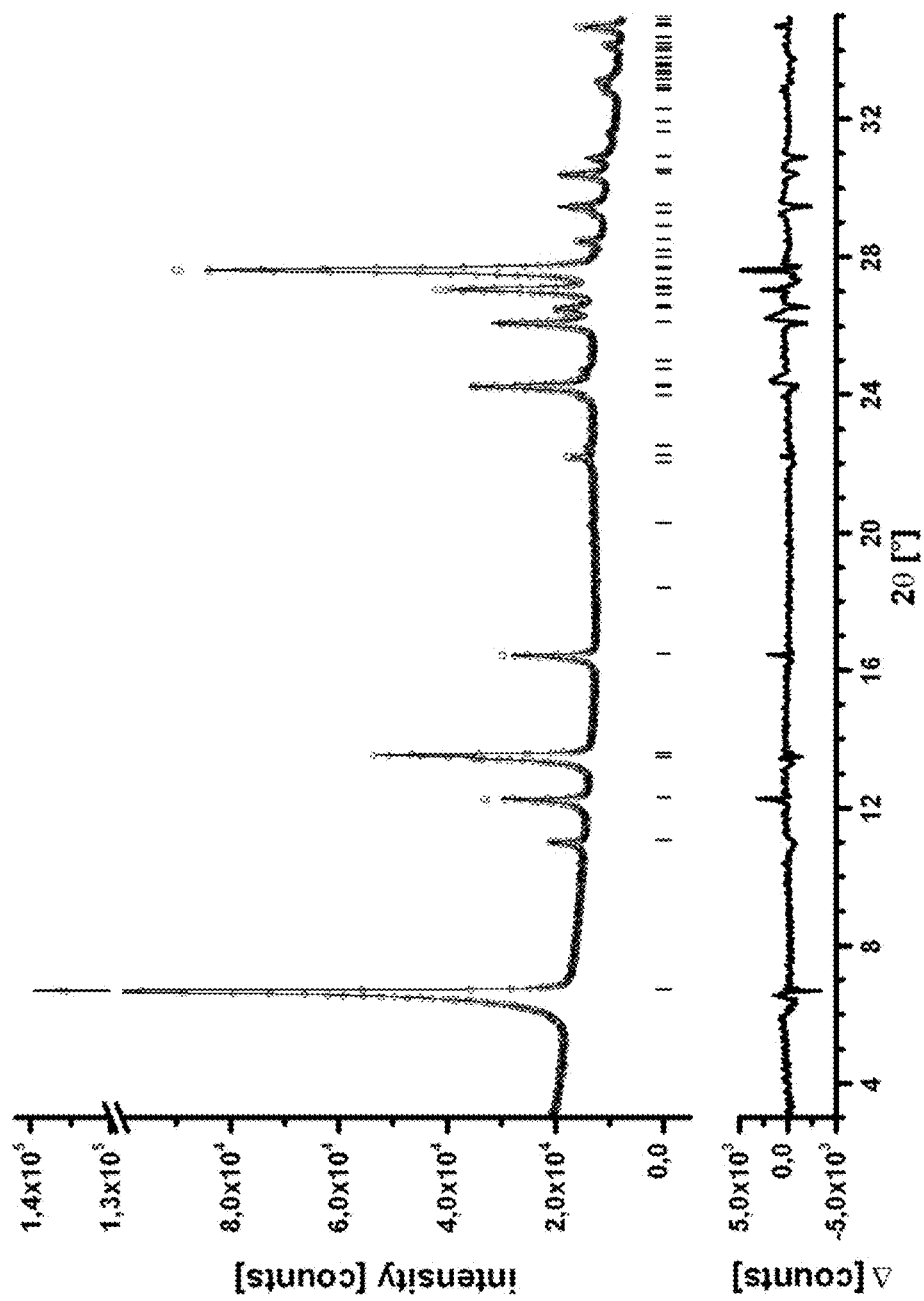
Figure 2A:
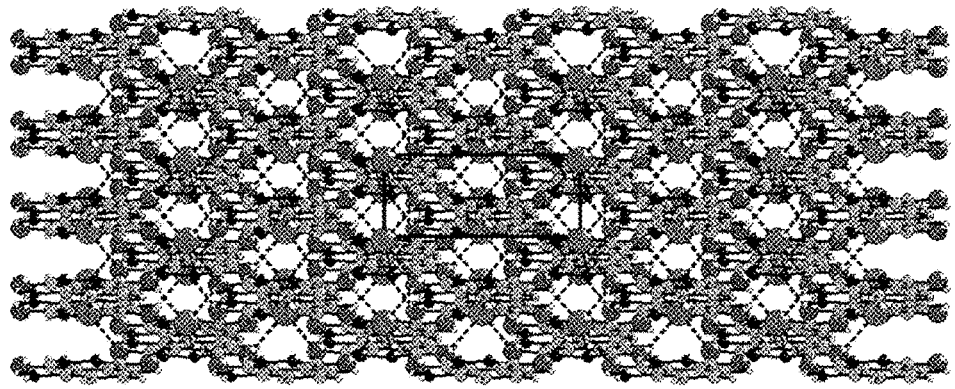
Figure 2A:
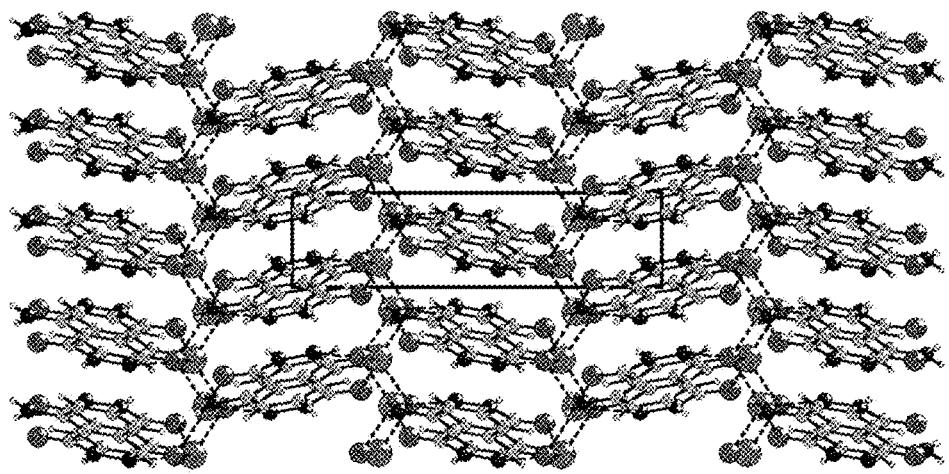
Figure 2A:
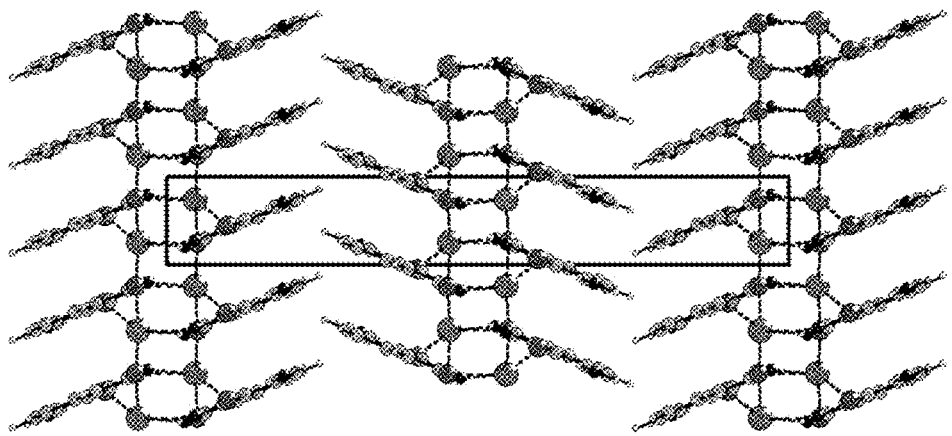
Figure 2B:
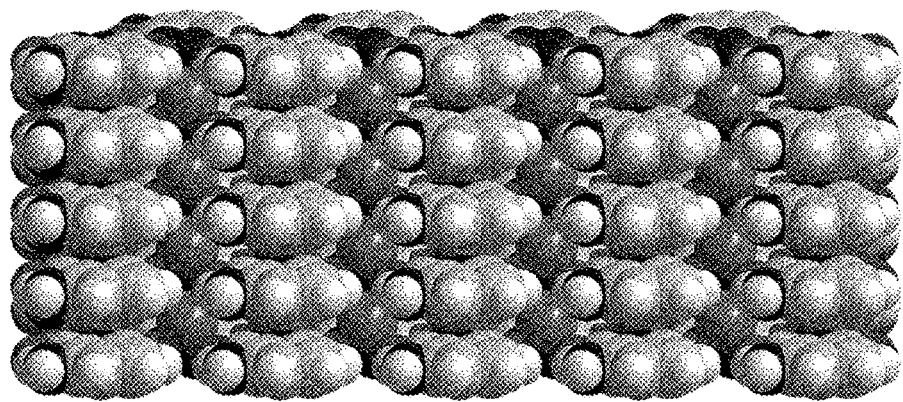
Figure 2B:
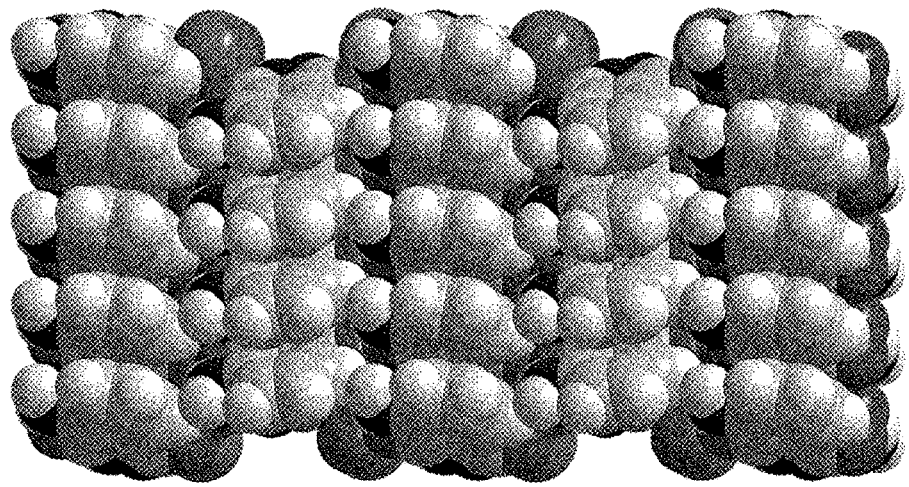
Figure 2B:
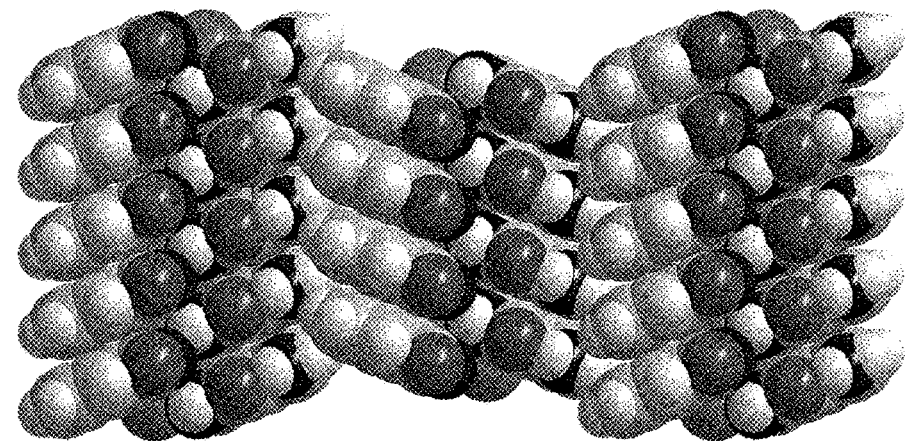
Figure 2C:
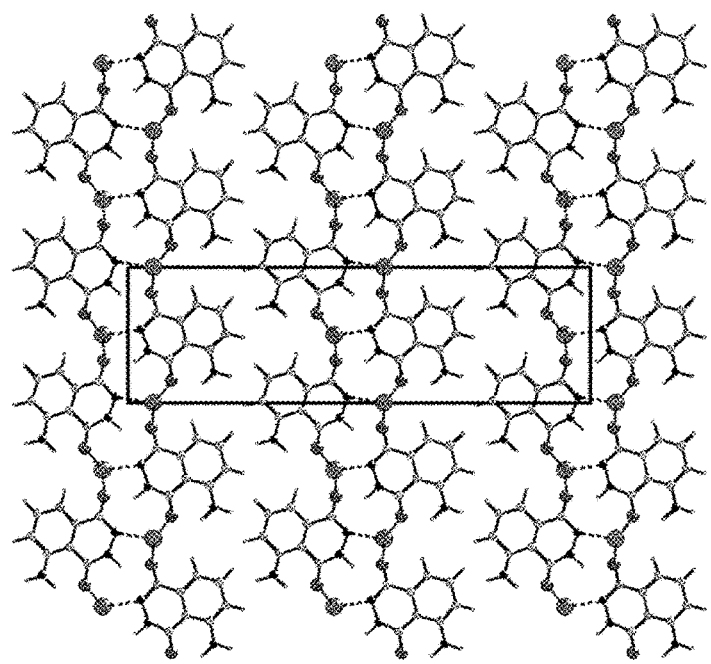
Figure 2C:
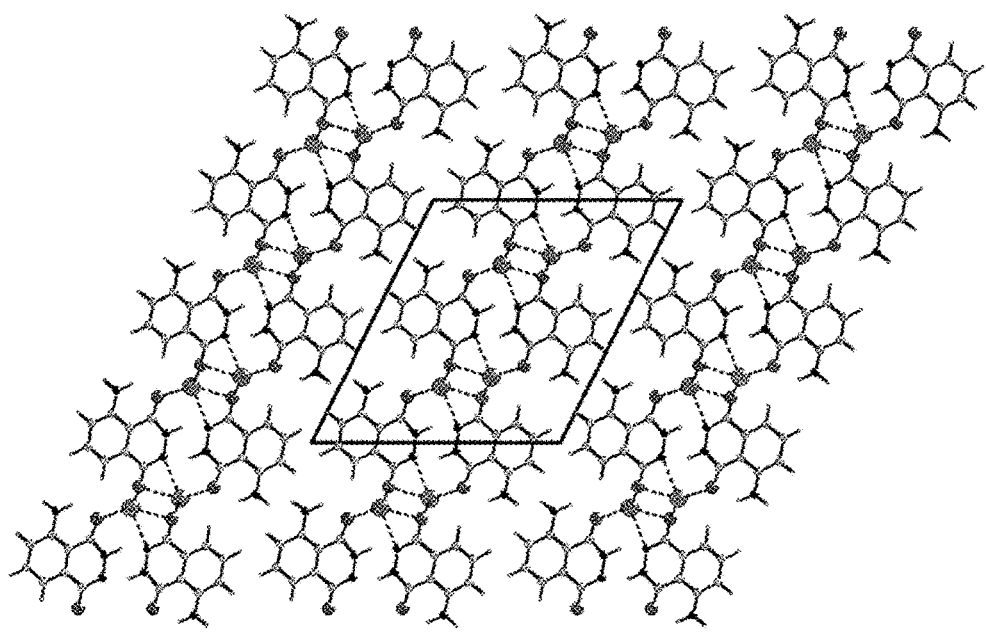
Figure 2C:
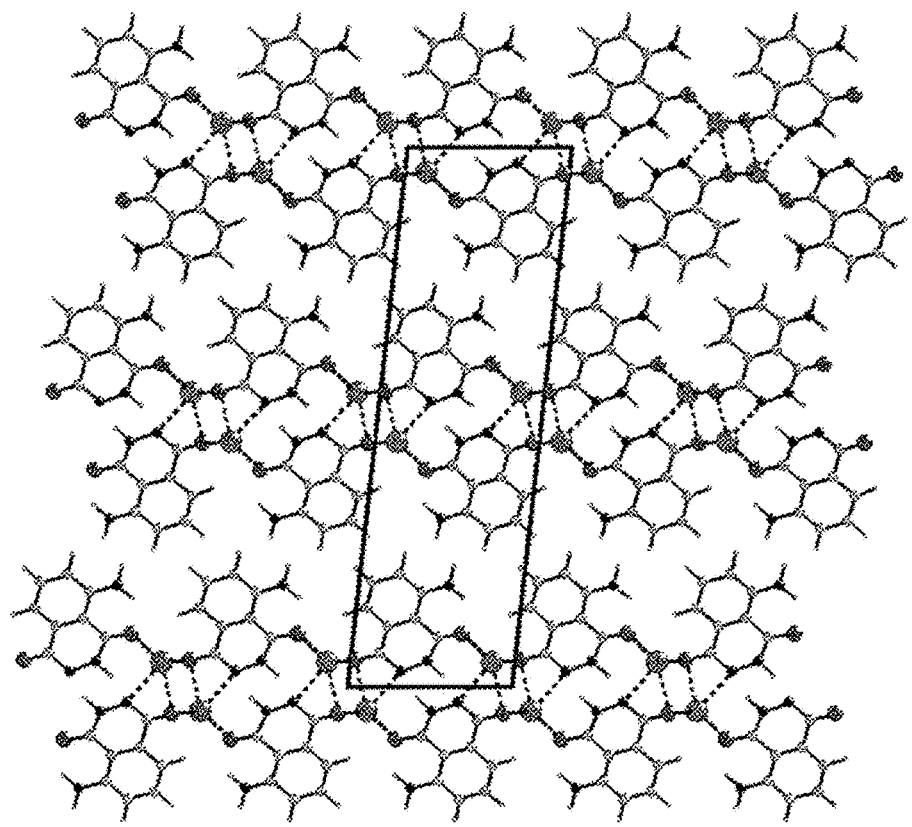
Figure 2D:
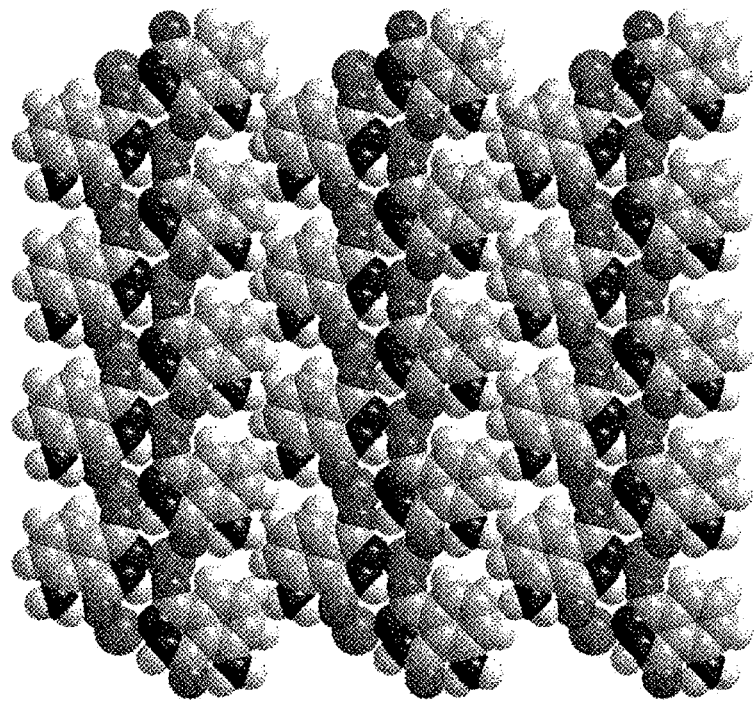
Figure 2D:
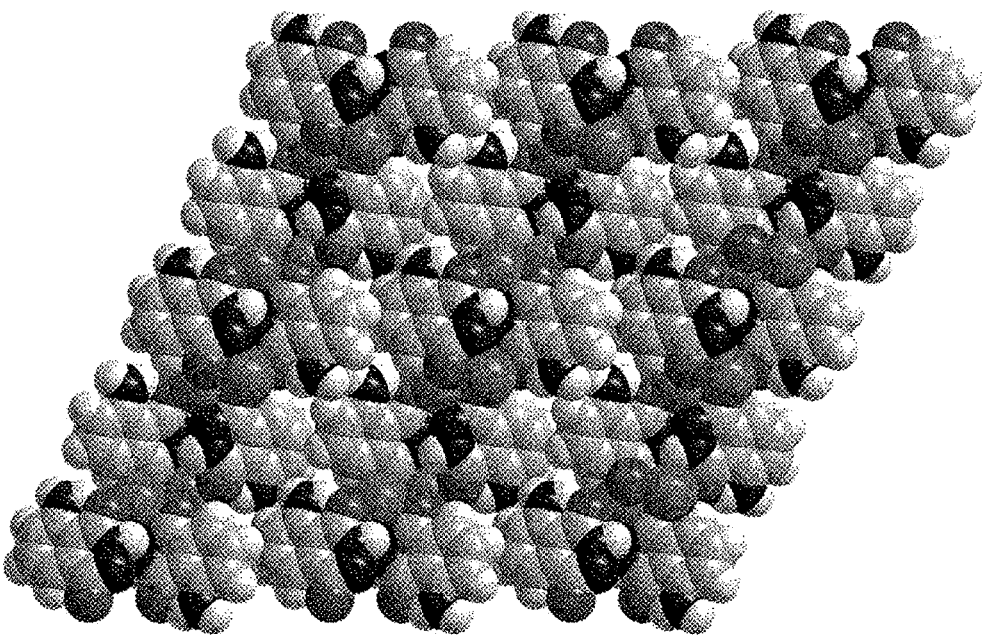
Figure 2D:
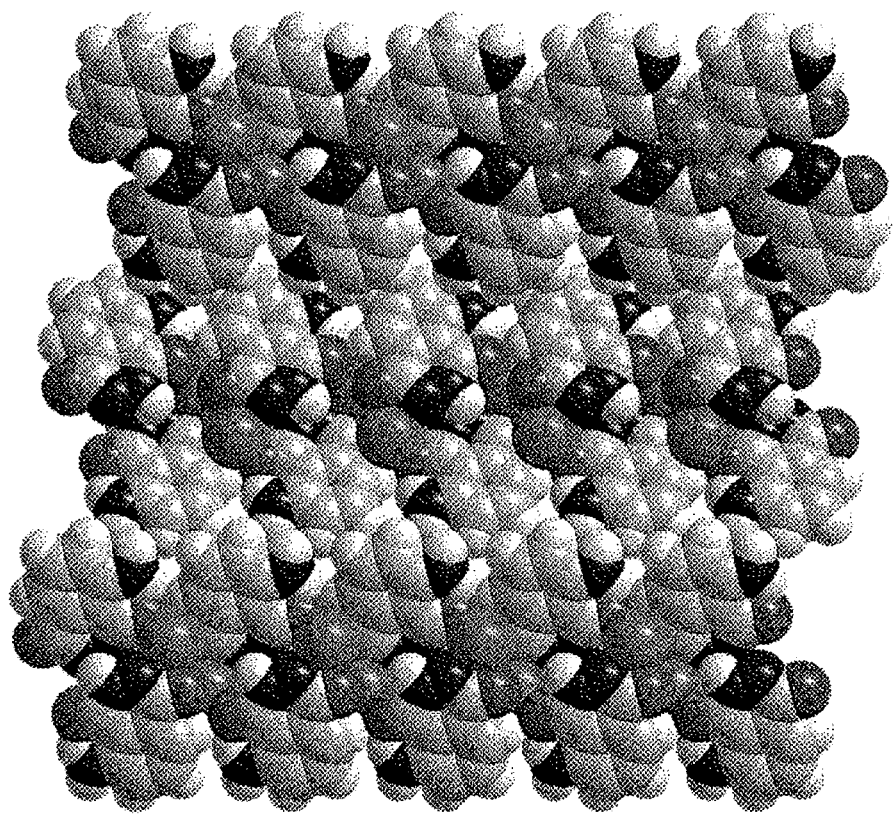
Figure 2E:
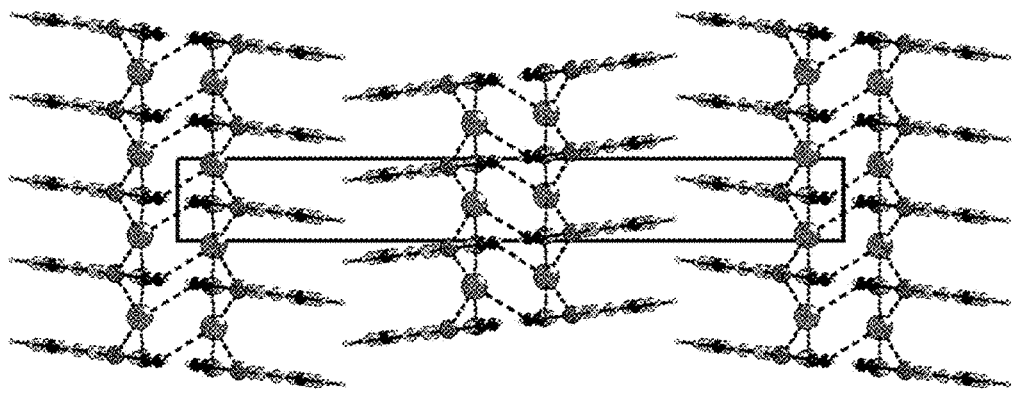
Figure 2E:
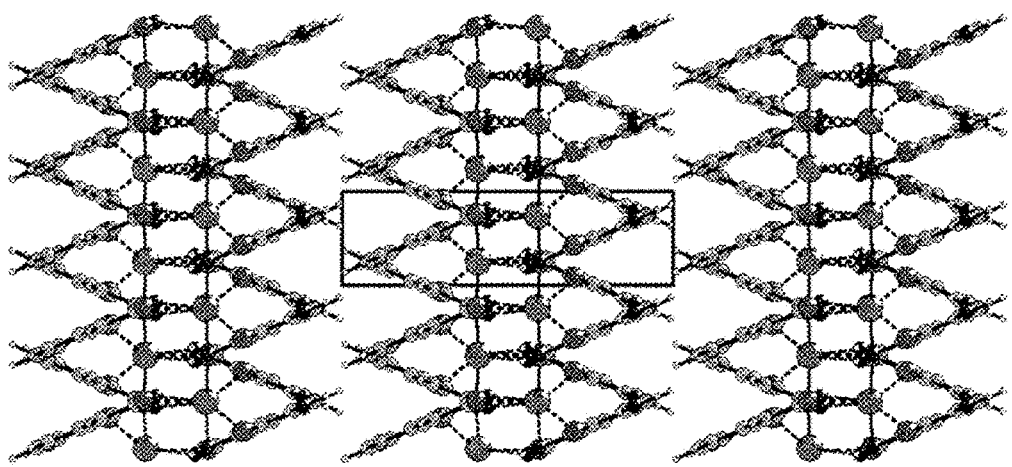
Figure 2E:
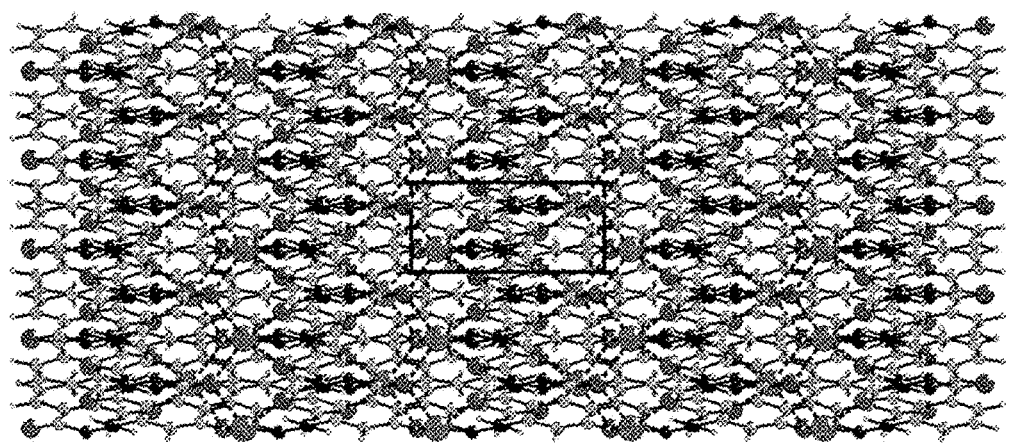
Figure 2F:
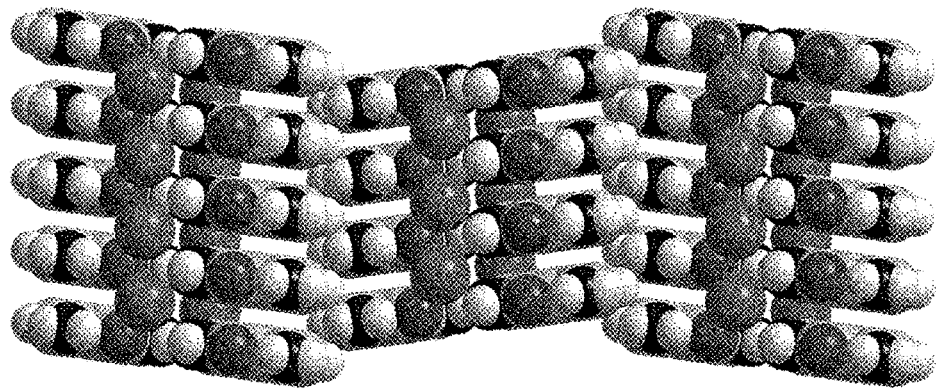
Figure 2F:
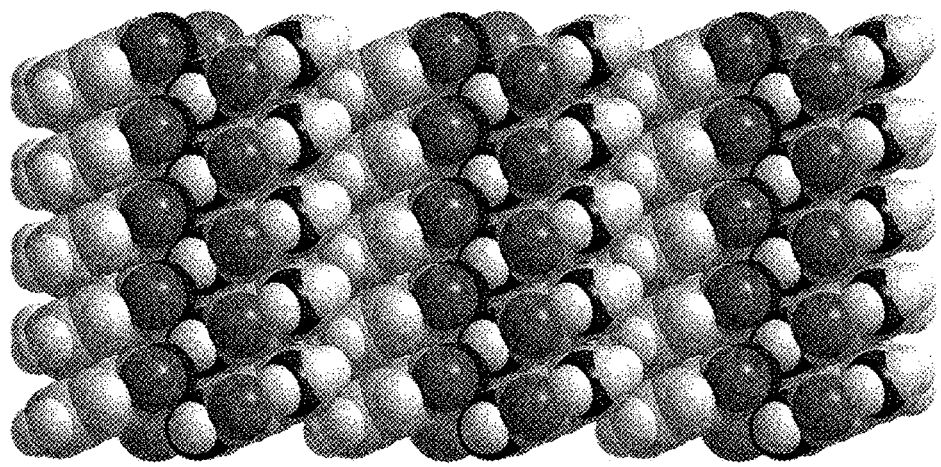
Figure 2F:
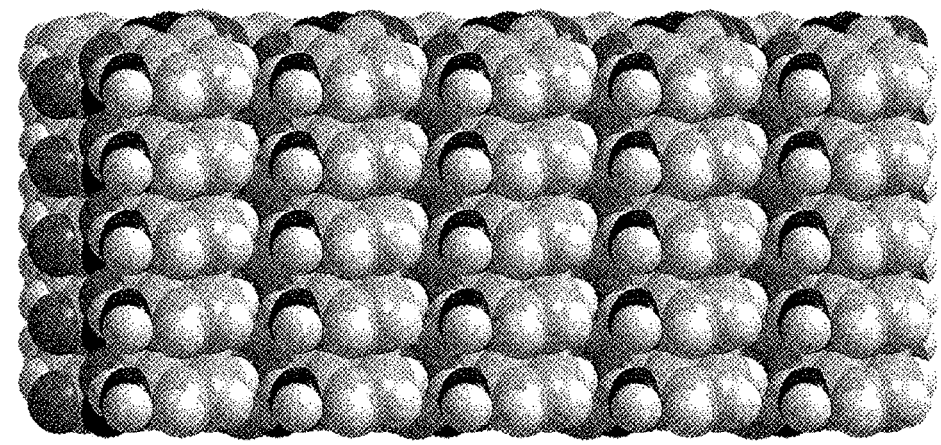
Figure 3A:
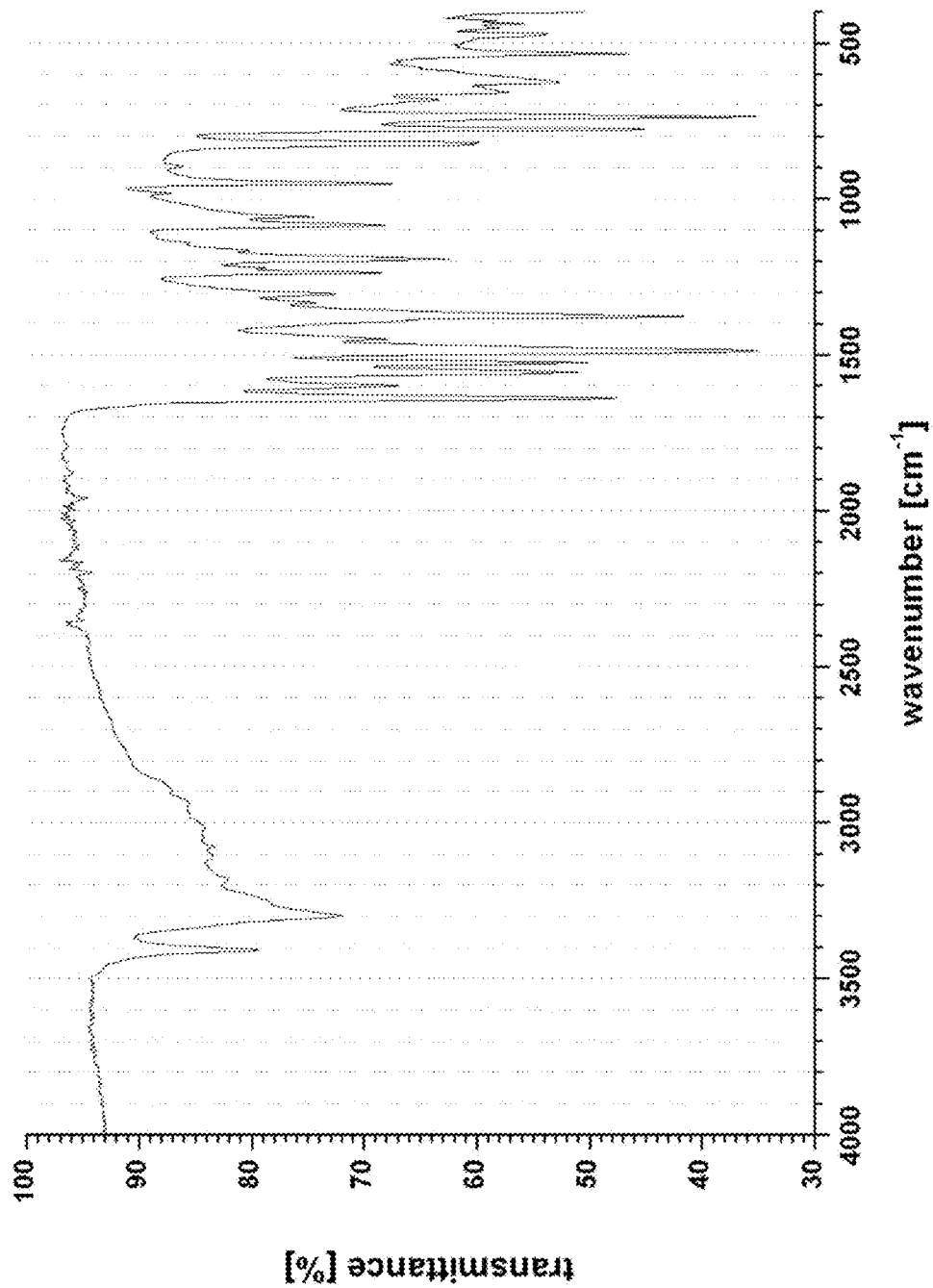
Figure 3B:
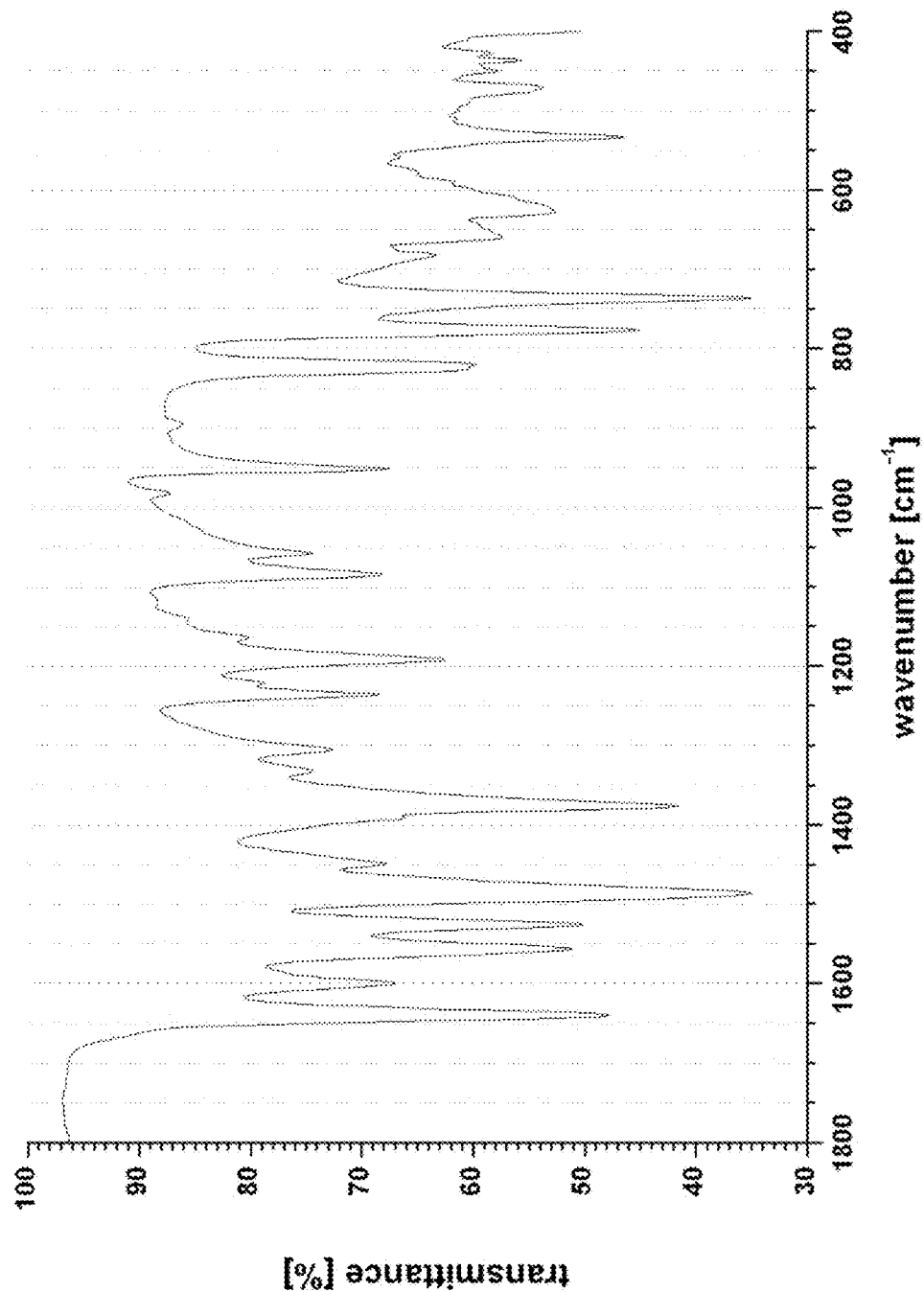

Form III according to the invention is further characterized by a solid state FT-IR spectrum, created with a JASCO FT/IR 6100 FT-IR spectrometer, provided with a DLATGS detector. The spectrum is expressed by graphically plotting the measured transmission in % and the respective wave number (FIG. 3).

Figure 4:
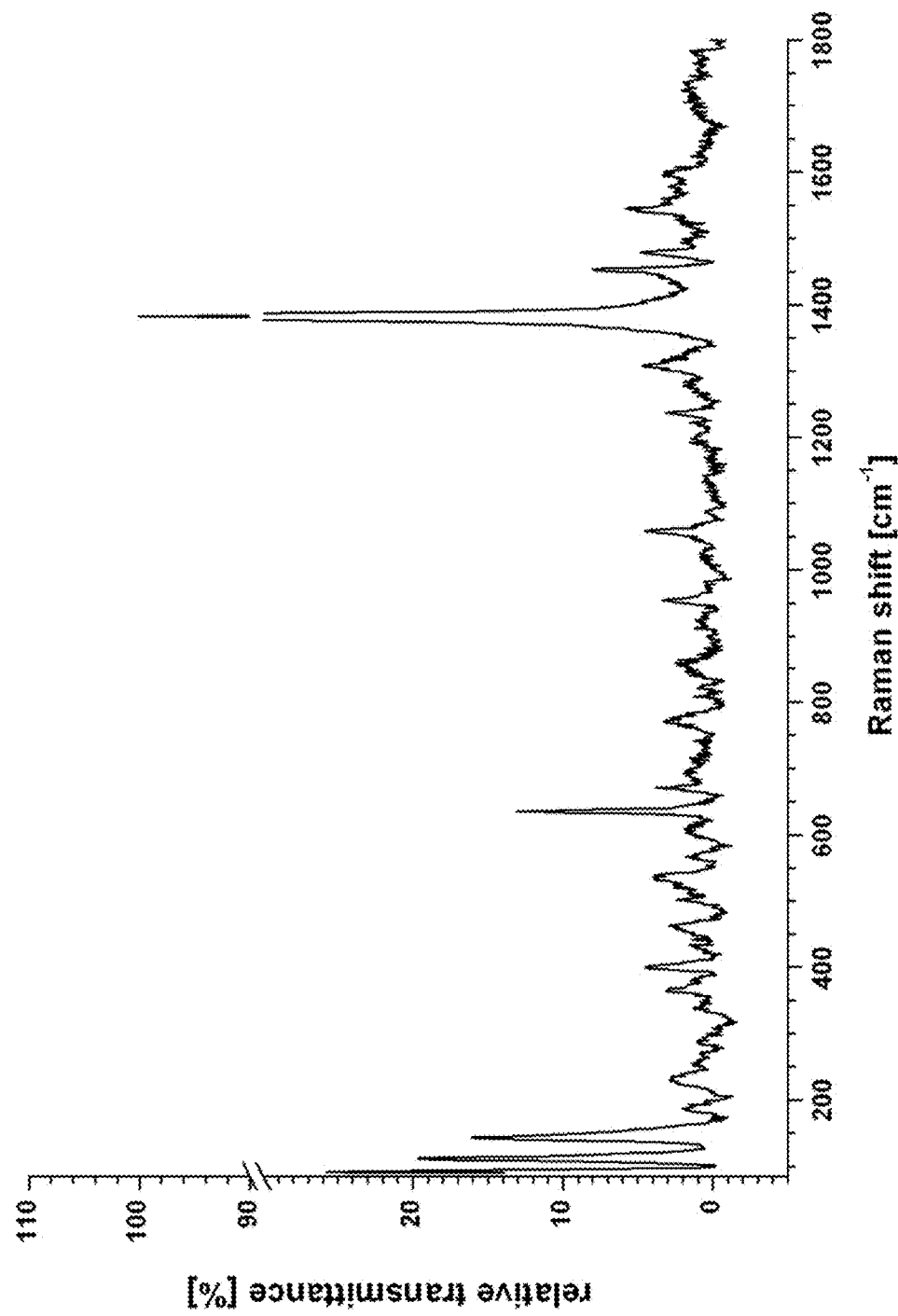
Figure 5A:
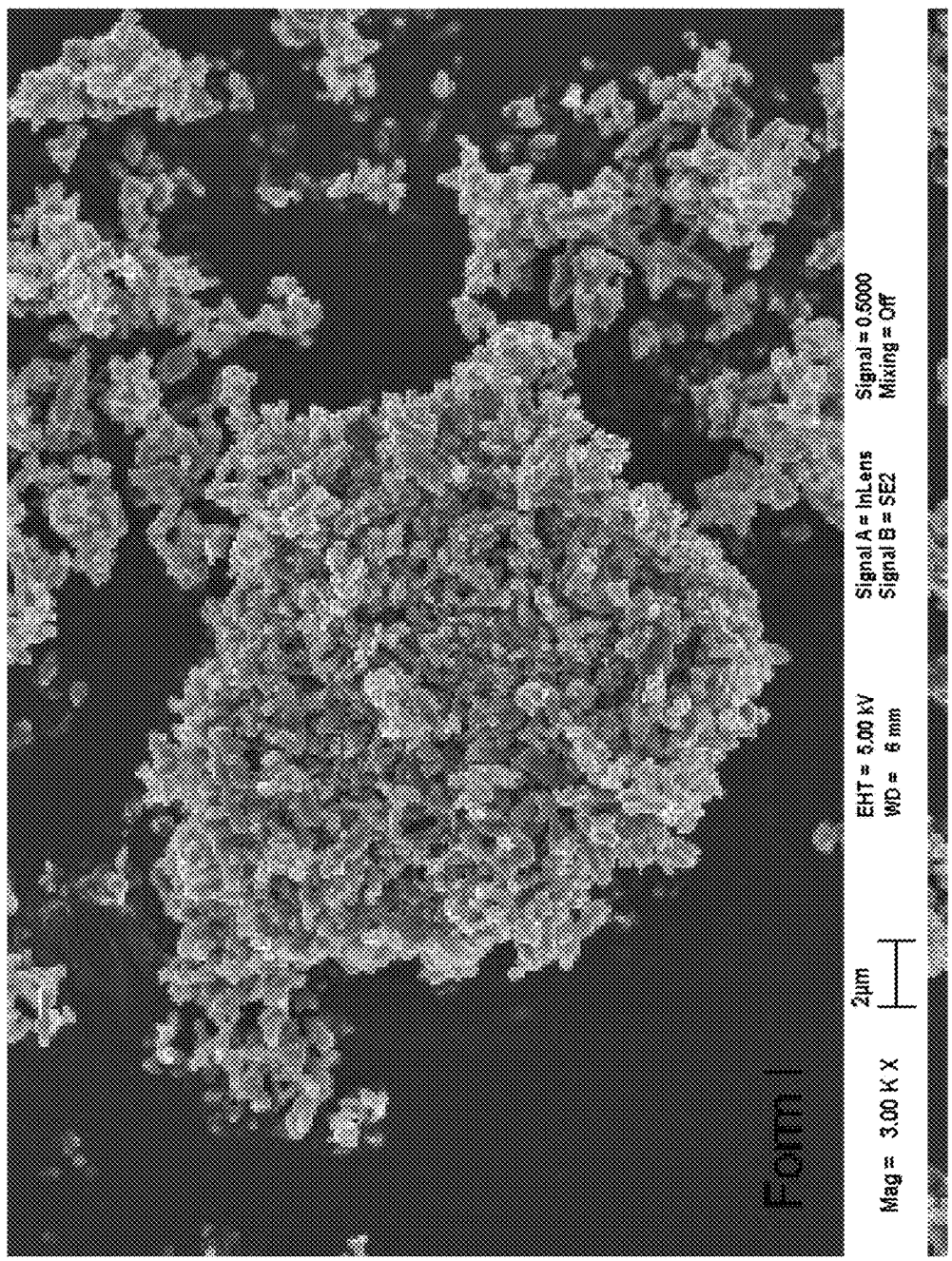
FIG. 5a shows a comparative presentation of all three forms in 2,500.times. magnification.
Figure 5A:
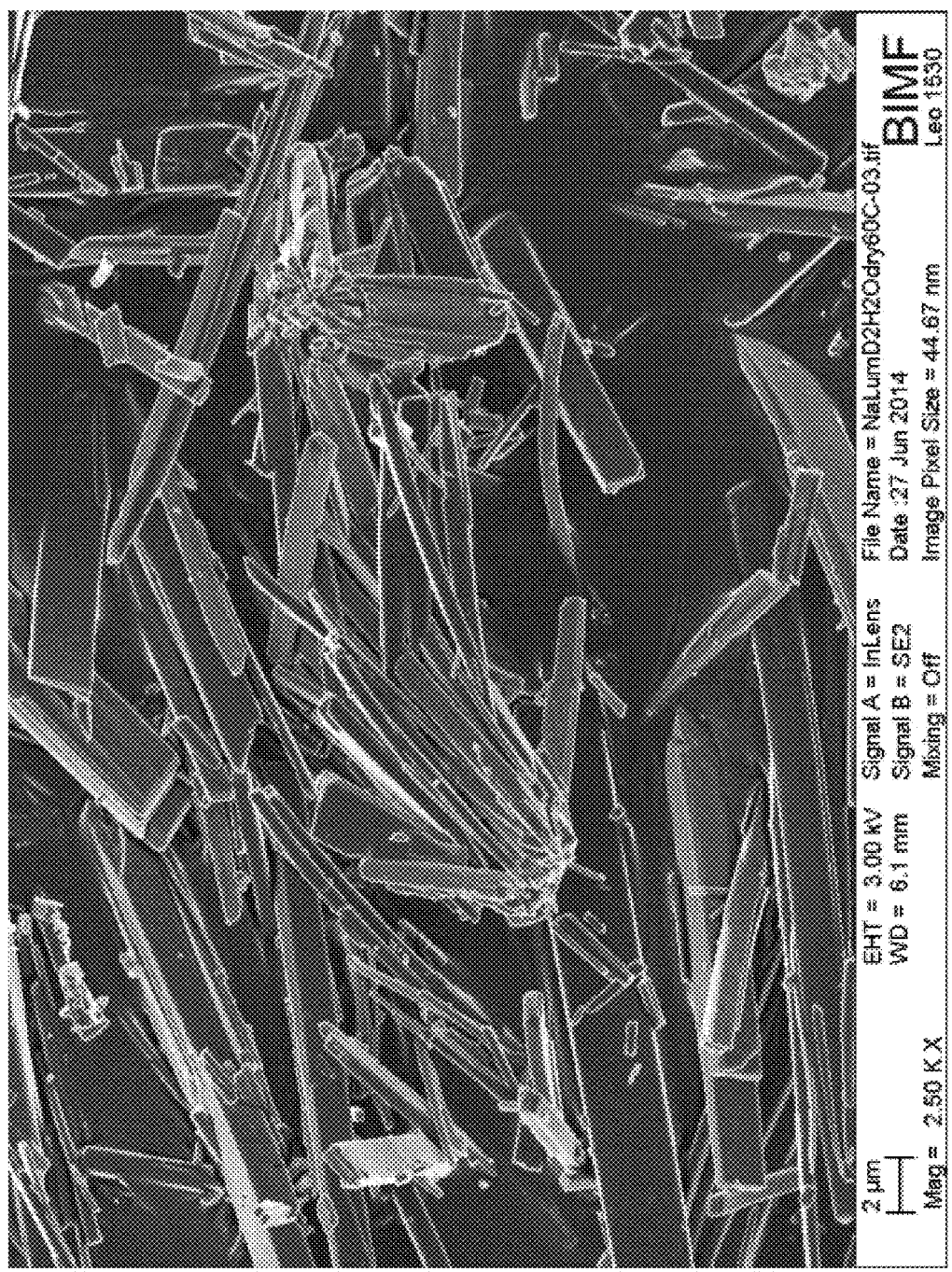
Figure 5A:
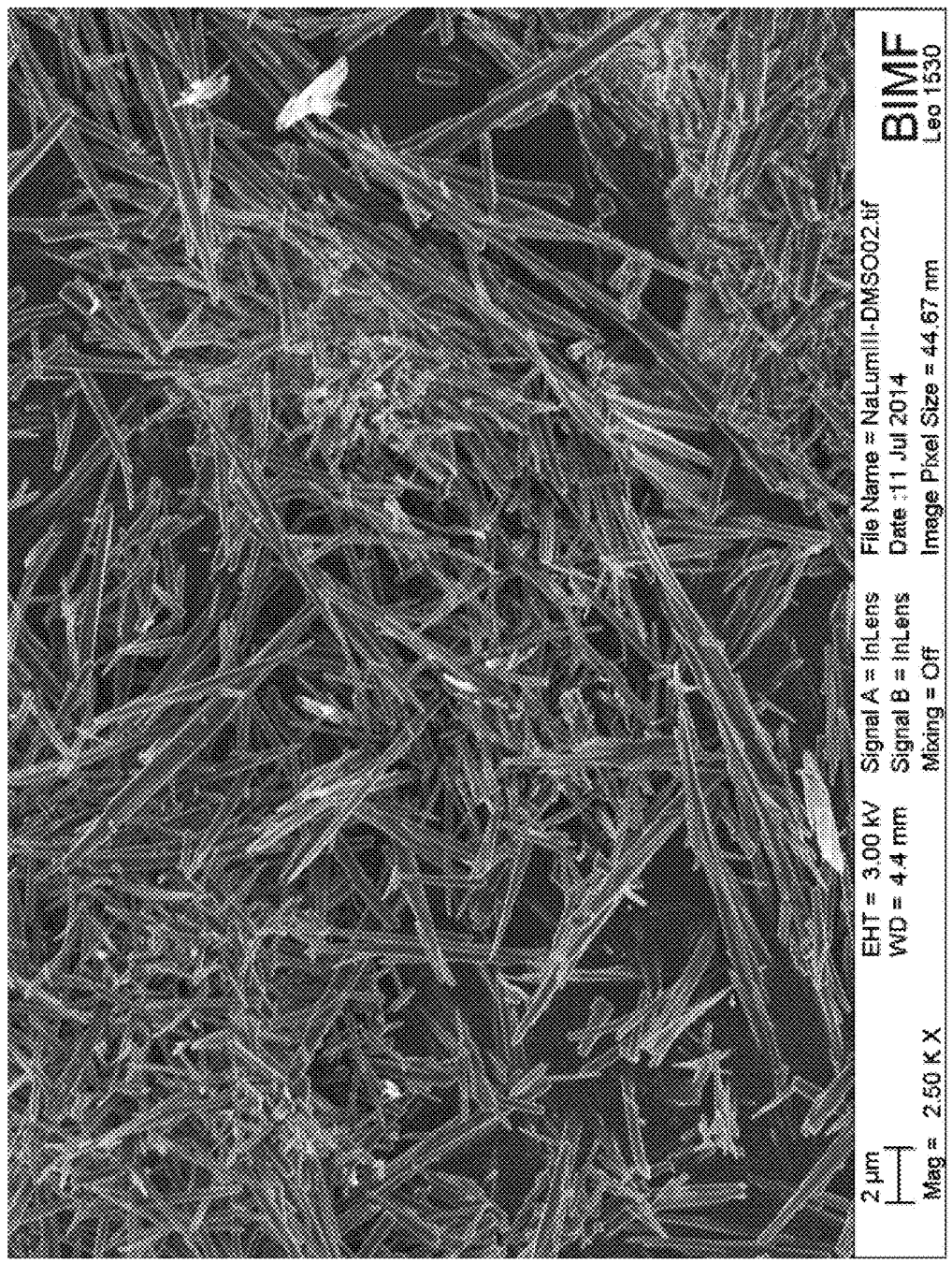
Figure 5B:
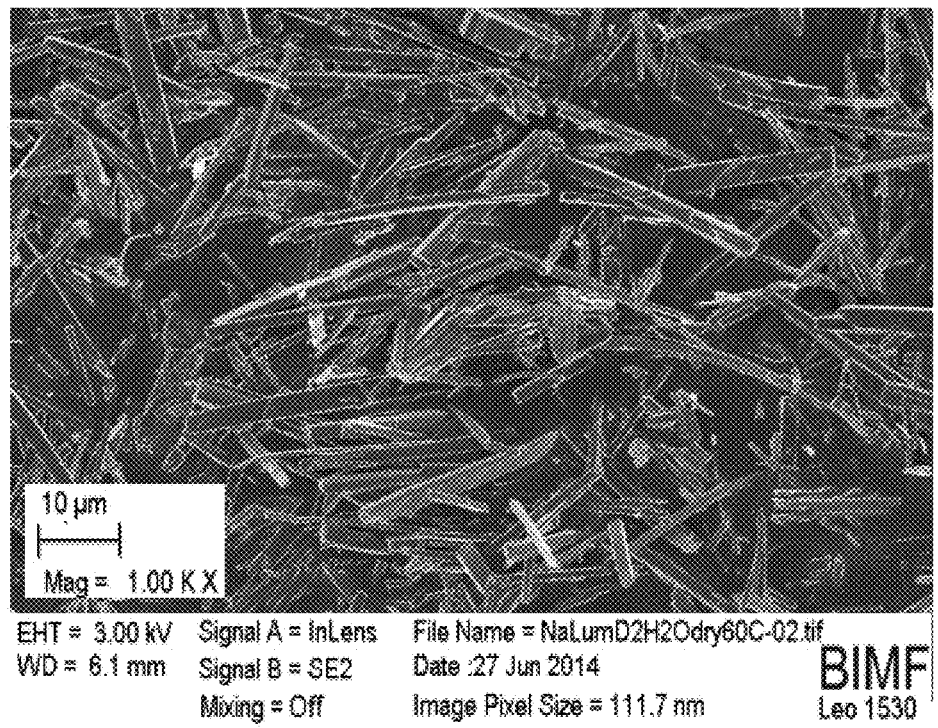
FIG. 5b shows a comparative presentation of the very similar forms II and III in 1,000.times., 10,000.times., 25,000.times. and 50,000.times. magnification.
Figure 5B:
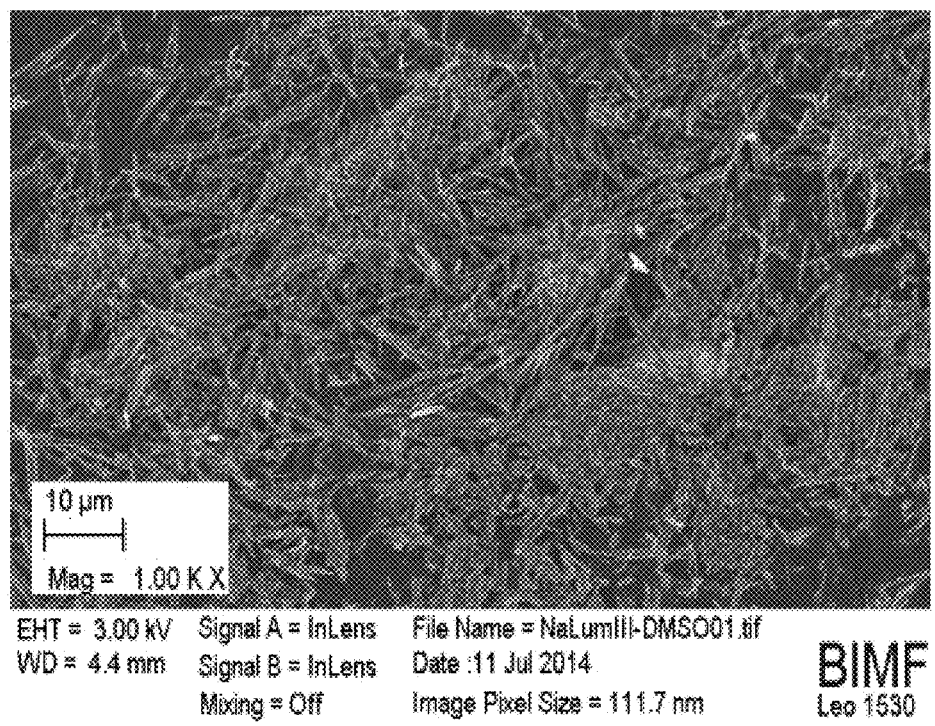
Figure 5B:
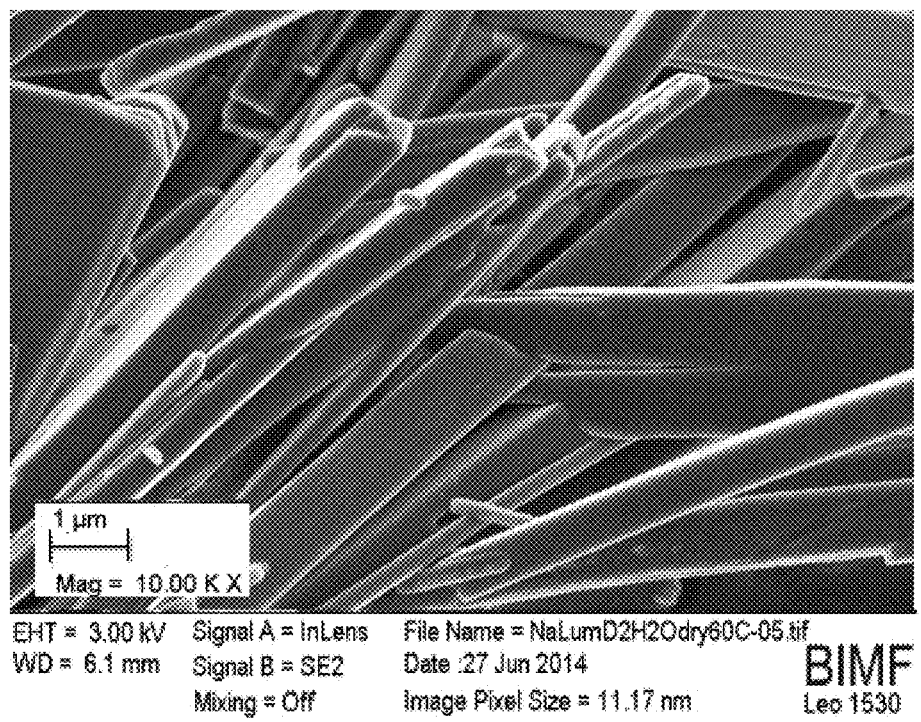
Figure 5B:
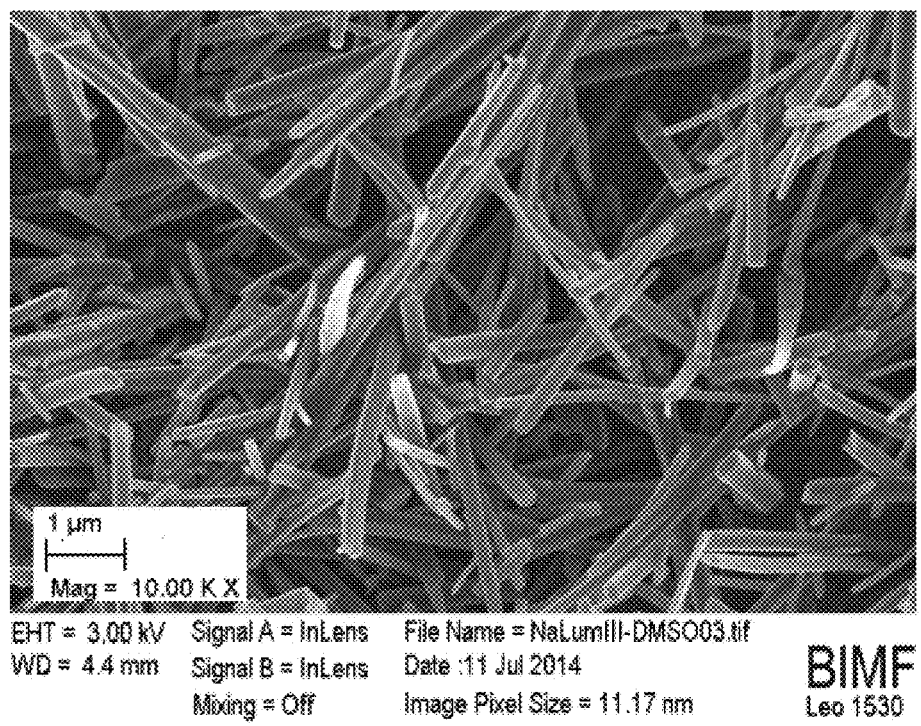
Figure 5B:
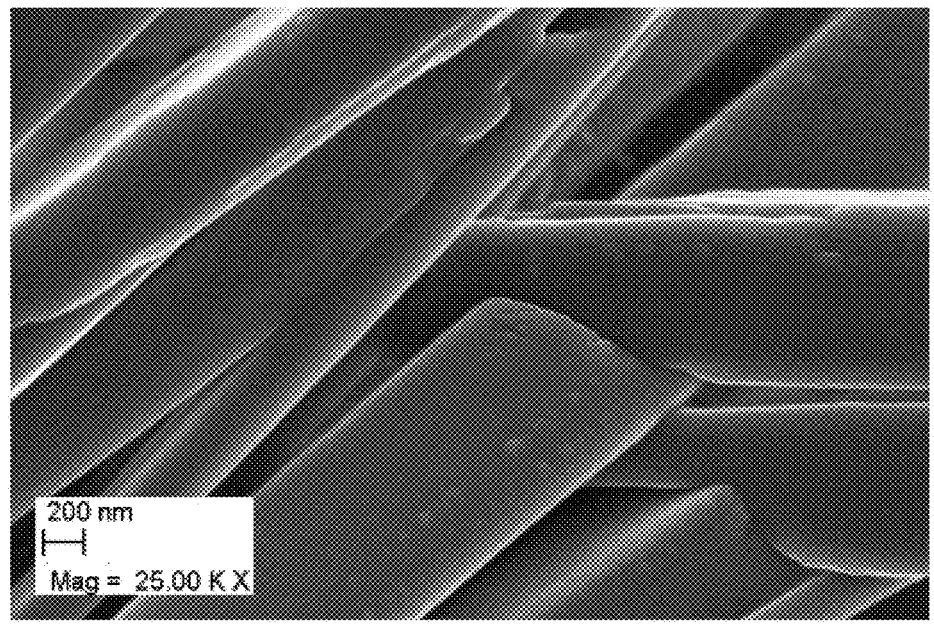
Figure 5B:
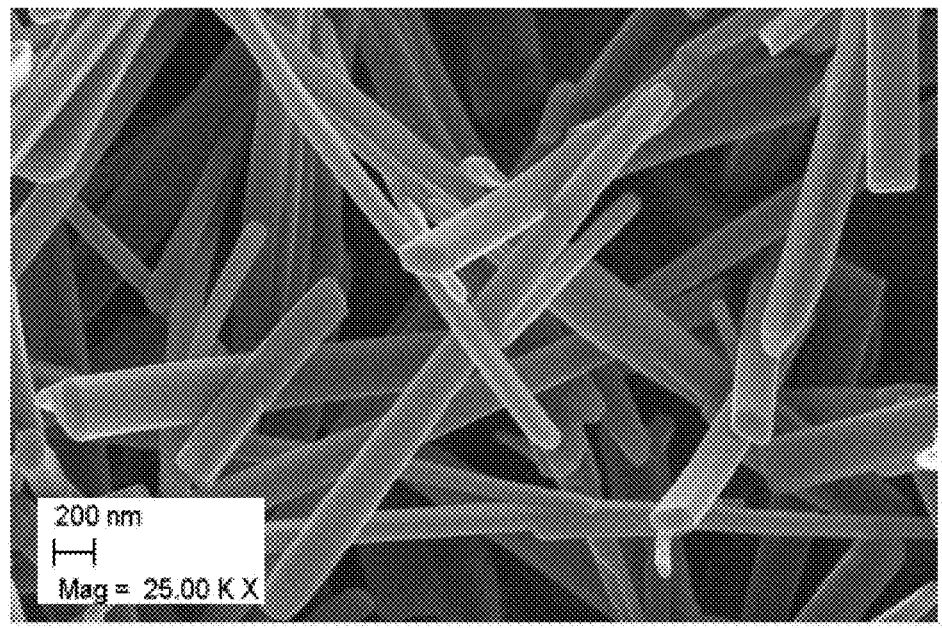
Figure 5B:
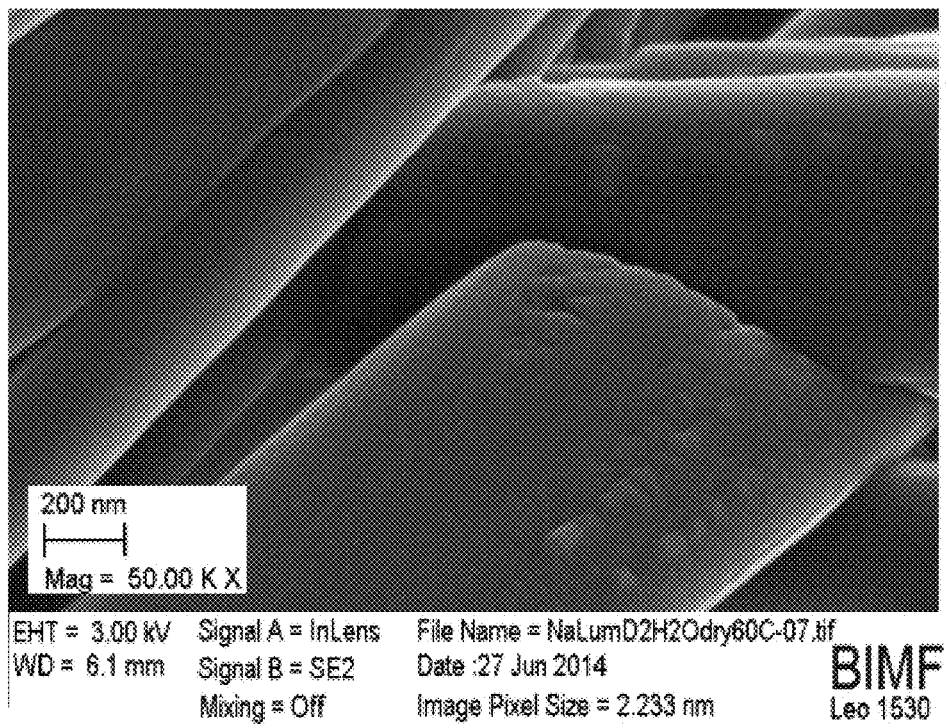
Figure 5B:
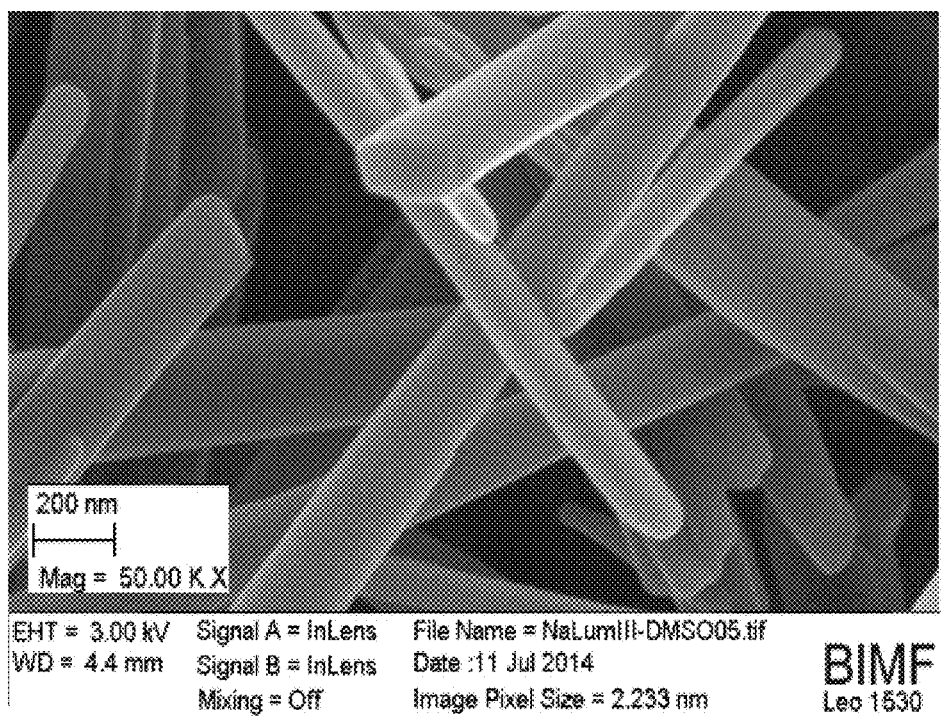

Form III according to the invention is further characterized by a Raman spectrum, created with a LabRam spectrometer with a resolution of 2 cm$^{-1}$, provided with a helium-neon laser (wave length 628.8 nm) and a 100× lens. The spectrum is expressed by graphically plotting the measured relative intensities in % and the respective wavenumber in cm$^{-1}$ (FIG. 4).

The anhydrate form III according to the invention preferably exhibits a content of water of crystallization of ≤0.4%.

Advantageous Physical Properties:

Surprisingly the inventors found that form III has advantageous physical properties for pharmaceutical processing and application, including thermostability, storage ability, solubility, bulk density, crystal form and phase purity. These are advantageous for the pharmaceutical production and further processing in comparison to for example hydrates (di-, tri- and hexahydrate), in which changes in water content can occur and thus formulation problems, for example due to weight changes of the active ingredient during tablet pressing, encapsulation or sterilization.

For use in medicine form III is advantageous over the mixed forms described by Rybakov et al. (2014: Crystallography Reports, 59, 383-393) because for pharmaceutical applications pure forms always are preferable over mixed forms as they can be better characterized and standardized. This is particularly important as different polymorphs can have different pharmacokinetic properties and thus a consistent bioavailability cannot be guaranteed in mixed forms.

The form according to the invention can be distinguished from known forms I and II by scanning electron microscopy: Form II primarily exhibits needle-like crystallites of octahedral structure with a length of several micrometers, which are built in layers; in the SEM of form II there are mainly morphologically inconsistent crystallites with rounded edges agglomerating in a powdery manner. The form III according to the invention also exhibits rather needle-like crystallites, however, in contrast to form II these crystallites have rounded edges at their tips (FIG. 5).

From its crystal form advantageous properties for the pharmaceutical processing arise for the form according to the invention: Due to their needle-like crystalline particles form II and form III are thus more suitable for direct tablet pressing. As crystallites of the form III according to the invention are significantly smaller than those of form II they provide—analogous to form I—an improved pourability and thus an improved filterability, as it is the case for form II. Also the bulk density of form III according to the invention is significantly higher than for form II (see Example 1).

It can thus be stated that form III according to the invention combines in itself the respective advantages of form II against form I and of form I against form II. Therefore form III has physical properties which provide a great advantage in the technical manufacture of medicinal products, in particular for the production of solid preparations such as tablets, capsules and powder. However, also within the scope of the production of liquid preparations these characteristics offer advantages due to the better manageability of the active ingredient according to the invention during the manufacturing process. Of particular note in this regard is the so called Hausner ratio, the quotient of bulk density and tapped bulk density. The closer the Hausner ratio is to 1 the less problems in controlling the dosing accuracy are to be expected. In particular for active ingredients with a big bulk volume, hence a low bulk density, one has to expect a significant difference between bulk volume and tapped bulk volume is to be expected, and accordingly the Hausner ratio is high. Otherwise, further steps subsequent to the production may become necessary, as e.g. grinding, air-flow crushing or sieving are thus not necessary for form III according to the invention. The provision of the hereto suitable equipment according to GMP requirements becomes irrelevant, and—generally expensive—production time is saved. This is a clear economic advantage.

As already described in WO2011/107295A1 for anhydrate forms form I and form II, the anhydrate form according to the invention also exhibits a very high thermostability with decomposition temperatures far above 300° C. Thus the decomposition of form III first starts from a temperature of 391.7° C.±10° C. The determination was carried out by means of simultaneous thermogravimetry (differential scanning calorimetry) at a Linseis L81-077 coupled with mass spectroscopy measurements with a Netzsch STA 449 C (thermobalance) with MS and FTIR coupling over 30-600° C. under synthetic air (4 N$_2$:1 O$_2$) and a heating rate of 10° C./min. The data were analyzed with the company software Proteus.

The thermoanalytical data confirm the assumption made by the inventors that crystalline form III as well as forms I and II exhibit advantageous characteristics with regard to stability and storage ability over the dihydrate having a solid phase transition at 85° C. (WO2011/107295A1). Also for other hydrates (e.g. trihydrate, hexahydrate) it is to be expected that a solid phase transition already starts below 100° C. This property further fosters the pharmaceutical processing of the crystalline form according to the invention by rendering said form insensitive to procedural steps with a high energy input, e.g. sterilization or grinding. In the manufacture of an active ingredient which allows terminal sterilization the GMP requirement of an closed sterile production over all procedural steps does not apply. This is a significant cost advantage.

The individual forms are also distinct from each other due to the different stoichiometric coordination of the sodium cation and the 5-amino-2,3-dihydrophthalazine-1,4-dione anion. Whilst in form I a sodium cation is coordinated by in total 6 5-amino-2,3-dihydrophthalazine-1,4-dione anions in a trigonal prism there are only 5 5-amino-2,3-dihydrophthalazine-1,4-dione anions in form II and III.

By use of Pauling's rules (cf. Linus Pauling (1929): Journal of the American Chemical Society, 51, 1010-1026) statements on the stability of ionically built crystal structures a.o. can be made. The third rule says that the occurrence of shared edges and particularly faces decrease the stability in the coordination polyhedra. Background to this is the electrostatic repulsion of cations which increases when the distance is reduced. Thus the sharing faces of the coordination polyhedra of adjacent cations in a crystal structure leads to a smaller distance between them than the sharing edges or corners of the coordination polyhedra.

In form I a sodium cation is coordinated by in total 6 5-amino-2,3-dihydrophthalazine-1,4-dione anions in a trigonal prism. This coordination leads to a face-bridging to two adjacent prisms, respectively, and to an effective distance of 3,395 Å between two adjacent sodium cations. In forms II and III a sodium cation is coordinated by 5 5-amino-2,3-dihydrophthalazine-1,4-dione anions with sharing edges with two directly adjacent polyhedra, respectively. This leads to an effective distance of 3.510 Å between two adjacent sodium cations in form II, and 3.578 or 3.595 Å between two adjacent sodium cations in form III, respectively.

Based on the third Pauling's rule and on the effective distances of the sodium cations it can therefore be assumed that the coordination of form III is more stable than the respective coordinations of form II and form I.

Moreover, crystalline form III appears substantially stable with regard to a change in the water content, therefore formulation problems due to weight changes of the active ingredient during subsequent pharmaceutical processing (e.g. tablet pressing, encapsulation) arise clearly less frequent.

The new crystalline form displays a further advantage over the prior art because the lower maximum solubility (Example 2) provides advantages in cases where a delayed release of the active ingredient is aimed at. Form III is thus particularly suitable for use in pharmaceutical preparations for oral and topical applications, in particular tablets, capsules, crèmes, powders and special retard formulations for applications in which a delayed release of the active ingredient is desirable.

Based on the results of "slurry" experiments (Example 3) it is to be expected that form III under normal storage conditions at room temperature is more resilient to transformation processes than form I and form II. According to GPP such transformation processes should only occur to a very small extent, or preferably not at all. Due to this advantage the storage ability (shelf life) of a medical product comprising form III is significantly increased, thus the usability and the value for the producing and/or distributing pharmaceutical industry is increased significantly. Furthermore, the demands on technical effort regarding storage are thus significantly decreased.

Example 1: Bulk Density

To compare bulk densities pure forms of the dihydrate and of form I, II and III were produced. Anhydrate form I for 5-amino-2,3-dihydrophthalazine-1,4-dione sodium salt produced according to the methods of WO2011/107295A1 served as starting material for the recrystallizations.

Production:

For the production of the dihydrate 10 g of 5-amino-2,3-dihydrophthalazine-1,4-dione sodium salt were solved in 100 mL $H_2O$ (demineralized) while stirring at room temperature until apparently there was no more turbidity. Subsequently, 900 mL 2-propanol were added to the solution. After the beginning precipitation the generated suspension was stirred for further 4 h. The suspension was filtered under vacuum utilizing a Büchner funnel. The remaining crystalline solid was dried at RT to constant mass.

The production of form I of 5-amino-2,3-dihydrophthalazine-1,4-dione sodium salt was carried out by solving 10 g of 5-amino-2,3-dihydrophthalazine-1,4-dione sodium salt in 100 mL $H_2O$ (demineralized) while stirring at room temperature until apparently there was no more turbidity. 900 mL 2-propanol were added to the solution. After the beginning precipitation the generated suspension was immediately filtered under vacuum utilizing a Büchner funnel. The remaining crystalline solid was dried at RT to constant mass.

The production of form II for 5-amino-2,3-dihydrophthalazine-1,4-dione sodium salt was carried out by solving 10 g of 5-amino-2,3-dihydrophthalazine-1,4-dione sodium salt in 100 mL $H_2O$ (demineralized) while stirring at room temperature until apparently there was no more turbidity. 900 mL 2-propanol were added to the solution. After the beginning precipitation the generated suspension was stirred for further 4 h. The suspension was filtered under vacuum utilizing a Büchner funnel. The remaining crystalline solid was dried at 60° C. in a drying cabinet to constant mass.

The production of form III of 5-amino-2,3-dihydrophthalazine-1,4-dione sodium salt according to the invention was performed as in production example 2—embodiment 1. 10 g of 5-amino-2,3-dihydrophthalazine-1,4-dione sodium salt were solved in 3.3 L DMSO while stirring at 90° C. until apparently there was no more turbidity. The solution was further stirred by applying a vacuum ($8\times10^{-3}$ mbar$\pm 1\times10^3$ mbar) at 90° C. until a suspension was generated. The suspension was dried at 90° C. under vacuum ($8\times10^{-3}$ mbar$\pm 1\times10^{-3}$ mbar) until a solid was generated. The solid was suspended in 2-propanol and filtered under vacuum utilizing a Büchner funnel. It was rinsed twice with 2-propanol. Subsequently, the crystalline solid was dried at 50° C. in a drying cabinet to constant mass.

After drying all forms produced were vortexed for 1 minute to let bigger agglomerates carefully disaggregate.

Measurement of Bulk Density:

To determine the bulk density of the dihydrate and of forms I and II as well as of form III according to the invention a hollow glass cylinder (height: 20 mm, diameter: 20.5 mm, volume: 6.601 $cm^3$; in the following referred to as "collecting vessel") with removable bottom was used. A sample of each of the respective solids to be determined was filled into a plastic funnel for solids (diameter of the outlet: 11 mm) with closable outlet which was mounted in a height of 20 mm above the collecting vessel. The funnel used was always filled half-full, thereby ensuring that there was always more sample material provided than necessary for filling the collecting vessel. After opening the outlet the respective solids trickled into the collecting vessel until it was filled up above the upper rim. The supernatant of the respective solids was removed with a spatula and the filled collecting vessel was weighed out with a high-resolution balance. The determination for each form was repeated 10 times and the mean value was calculated (Table 3).

Results:

Form III exhibits a higher bulk density compared to the anhydrate forms known so far as well as compared to the dihydrate, whereby the difference in bulk density is highly significant compared to the dihydrate and also to form II ($p<0.001$, t-test, unpaired, 2-tailed).

TABLE 3

| Bulk densities [kg/$m^3$] of forms I-III and of the dihydrate (mean ± standard deviation) | | | |
| --- | --- | --- | --- |
| Form I | Form II | Form III | Dihydrate |
| 201.9 ± 3.9 | 108.6 ± 3.0 | 203.5 ± 6.7 | 72.3 ± 4.1 |

Example 2: Maximum Solubility in Water at RT

The maximum solubility of crystalline form III in water at RT—until a saturated solution is generated—was determined. Accordingly, form III with a value of 145 mg/mL is less soluble than forms I and II (cf. WO2011/107295A1).

Determination of the maximum solubility of crystalline form III in water at RT was carried out with UV-Vis spectroscopy in an Agilent Cary 300 UV-Vis spectrometer.

This process is based on a linear correlation between the concentration of a dissolved solid and the calculated absorption at a particular wavelength (Beer-Lambert law).

A stock solution of 0.502 g of form III in 2 mL $H_2O$ (demineralized) was produced. For the generating a 3-point calibration curve three solutions were produced after appropriate dilution thereof with concentrations of 0.5041 mmol/l, 0.2521 mmol/l and 0.1260 mmol/l, and their respective absorption at 347 nm was determined. At this wavelength 5-amino-2,3-dihydrophthalazine-1,4-dione sodium salts exhibit an absorption maximum in the UV spectrum. Further, a supersaturated solution of 0.531 g of form III in 2 mL $H_2O$ (demineralized) was produced to determine the maximum concentration. 100 µL of the solution were 2000-fold diluted and the absorption at 347 nm was determined as well.

Accordingly, the calculated value for the maximum solubility of form III in water at RT was 145 mg/mL (this corresponds to a maximum concentration of 0.73 mol/l).

Example 3: Slurry Experiments

In polymorphs of crystalline solids phase transitions occur depending on the thermodynamic stability of the individual forms. Herein applies that the thermodynamically less stable (metastable) form transforms into the thermodynamically more stable form. Different transformation processes are known. There are solid phase transitions—where an energy input (temperature, pressure, etc.) into a phase mixture induces the transition of the thermodynamically less stable into the more stable form—and solvent-induced phase transitions—where the dissolution of the metastable form takes place in favor of crystal nucleation and crystal growth of the stable form. In this respect so-called slurry experiments can provide information on the thermodynamic stability of polymorphs of a solid.

To compare the stability under the influence of solvents 50:50 (wt %) solid phase mixtures were produced of form III according to the invention and form I as well as of form III according to the invention and form II.

In each case 0.05 g of the respective solid phase mixture were suspended in 5 mL 2-propanol, methanol or ethanol, respectively. The mixture of form III and form I was stirred at RT for 3 days. The mixture of form III and form II was stirred at RT for 24 h. The suspensions were filtered under vacuum utilizing a Büchner funnel. The remaining crystalline solid was completely dried at RT. X-ray powder diffraction patterns of the resulting crystalline solids were recorded with a Bragg-Brentano diffractometer (STOE STADI P) provided with a DECTRIS MythenlK detector using mono-chromatized (Ge111-monochromator) copper emissions Cu K($\alpha$1) (wave length $\lambda$=1.54187 Å).
Results:

After stirring for 24 hours a significant intensity increase of reflections showed for the mixture of form II and form III in the recorded X-ray powder diffractograms with all solvents which can clearly be assigned to form III (FIG. 6a). Therefore it must be assumed that form III is the thermodynamically more stable polymorph at RT in comparison to form II.

After stirring for 3 days a significant intensity increase of reflections showed for the mixture of form I and form III in the recorded X-ray powder diffractograms with all solvents, which can clearly be assigned to form III (FIG. 6b). According to these results form III is likewise the thermodynamically more stable polymorph at RT in comparison to form II.
Biological Efficacy The biological efficacy of 5-amino-2,3-dihydrophthalazine-1,4-dione sodium salt has been repeatedly proven in the past.

The comparable biological efficacy of form III compared to form I and II and the dihydrate could be shown in vitro in LPS-induced HL60 cells (Example 4).

Example 4—Differentiated HL60 Cells

For example, it is known from WO2011/107295A1 that both form I as well as form II are able to reduce the secretion of cytokines, in particular of TNF alpha and IL-6, both in vitro as well as in vivo. This could now be confirmed in an in vitro model for form III as well. Not only the forms already known but also the form III according to the invention leads to a reduction of the cytokine secretion in a model with LPS-induced HL60 cells (human promyelocytic leukemia cells) which were differentiated to macrophages.

For the differentiation to macrophages HL60 cells were treated with phorbol 12-myristate 13-acetate (PMA) in advance. Subsequently, the cells were pre-stimulated with 1 mmol/l dihydrate, form I, II or III, respectively, before 100 ng/mL lipopolysaccharides (LPS) were added for 24 hours. Said amount of LPS without prior adding of the active ingredient was used as control (100%). The secretion of TNF alpha and IL-6 was determined in the cell supernatant using ELISA testing over 3 measurements, respectively. Table 4 as well as FIGS. 7a and 7b show the respective mean value m and the standard deviation s (GraphPad Prism 5).

The dihydrate of 5-amino-2,3-dihydrophthalazine-1,4-dione sodium salt as well as the anhydrate forms form I, II and III all showed a more or less clearly decreased secretion of TNF alpha and IL-6 in HL60 cells. Therefore form III has a biological efficacy comparable to the dihydrate and forms I and II.

TABLE 4

TNF alpha and IL-6 secretion in LPS-stimulated HL60 cells

| Form | TNF-alpha (pg/mL) | | IL-6 (pg/mL) | |
| --- | --- | --- | --- | --- |
| | m | s | m | s |
| Control | 30.08 | 3.56 | 42.81 | 2.29 |
| Dihydrate | 26.87 | 0.68 | 40.93 | 2.29 |
| Form I | 25.28 | 4.29 | 41.15 | 1.10 |
| Form II | 22.16 | 0.90 | 36.11 | 3.27 |
| Form III | 22.15 | 4.69 | 34.86 | 2.98 |

Thus it could be demonstrated in a standard in vitro system that form III of 5-amino-2,3-dihydrophthalazine-1,4-dione sodium salt according to the invention has an equivalent or even better biological efficacy concerning the essential inflammatory markers TNF alpha and IL-6 when compared with the known forms I and II and the dihydrate. Hence in therapeutic use an equivalent or better effect compared to prior art is to be expected.

Production of the Crystalline Form According to the Invention

In the following the manufacturing of crystalline form III is described exemplarily.

Starting material for the synthesis is 5-amino-2,3-dihydrophthalazine-1,4-dione known from prior art, which for example can be produced according to the following reaction scheme:

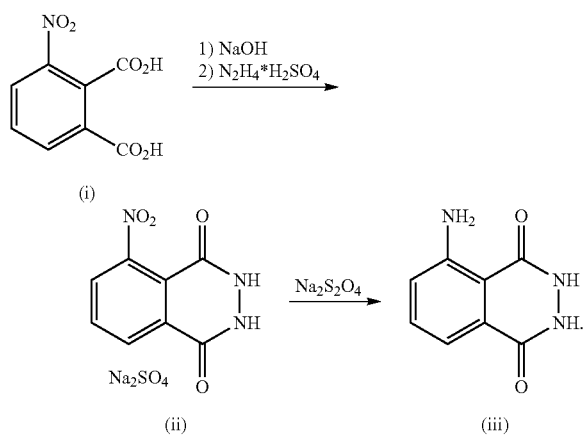

Depicted is the synthesis of 5-amino-2,3-dihydrophthalazine-1,4-dione (iii) by reacting 3-nitrophthalic acid (i) which in an alkaline medium can be reduced via 3-nitrophthalanhydride to 5-amino-2,3-dihydrophthalazine-1,4-dione (ii) with hydrazine or one of its salts or any other suitable reducing agent, e.g. ammonium sulfite or triethylene glycol. Suitable production processes for 5-amino-2,3-dihydrophthalazine-1,4-dione can be found in Williamson, K. L. In: Macroscale and Microscale Organic Experiments; $2^{nd}$ ed.; D. C. Heath: Lexington, Mass., 1994. A further suitable method for the production of 5-amino-2,3-dihydrophthalazine-1,4-dione which uses a Raney nickel catalyst can e.g. be found in U.S. Pat. No. 6,489,326 B1.

A preferred more specific method for a production independent of the amount of the starting material 5-amino-2,3-dihydrophthalazine-1,4-dione is described in WO2011/107295A1: Herein 1 equivalent of 3-nitrophthalic acid and 1.1 equivalents of hydrazine hydrate are provided and mixed with 1.5 equivalents of ethylene glycol. In parallel, the temperature is raised up to 110-200° C. and water is removed by distillation. When no more water is built the mixture is cooled down to 100° C. and 6 equivalents water are added. After cooling the mixture to room temperature and stirring over night the precipitate is filtered, washed with water and then dried to constant mass.

Subsequently, anhydrate form I or II of 5-amino-2,3-dihydrophthalazine-1,4-dione sodium salt can be produced by mixing 5-amino-2,3-dihydrophthalazine-1,4-dione in sodium hydroxide and dropwise adding this solution into a low-molecular liquid alcohol which lowers the solubility product of the generated 5-amino-2,3-dihydrophthalazine-1,4-dione sodium salt in such a way that the latter starts to precipitate. The precipitate generated by precipitation is dried thereafter. WO2011/107295A1, for example, provides various detailed methods for the production of anhydrate forms I and II.

Subject-matter of the present invention are also methods for the production of anhydrate form III by solving any anhydrate form of 5-amino-2,3-dihydrophthalazine-1,4-dione sodium salt (pure form or mixture) at at least 90° C. while stirring in DMSO (dimethyl sulfoxide). Stirring is continued until—approximately after one hour—the solution is completely clear. Thereafter the solution is stirred further on at constant temperature as possible (+20° C.) until a suspension is generated. Subsequently, the solution is—without stirring—further held at constant temperature (±20° C.) as possible until DMSO is completely evaporated. The methods are further specified in the following production examples.

Production Example 1—Embodiment 1

A possible production of form III comprises the addition of any anhydrate form (form I, form II, or a mixture of form I and form II) of 5-amino-2,3-dihydrophthalazine-1,4-dione sodium salt to DMSO at a weight ratio of 5-amino-2,3-dihydrophthalazine-1,4-dione sodium salt to DMSO from 1 to 300 up to 1 to 30,000; preferred from 1 to 300 up to 1 to 3,000; particularly preferred from 1 to 300 up to 1 to 350. The mixture is stirred until complete dissolution—i.e. until apparently there are no more turbidities—at a temperature from 90° C. to 189° C., preferably from 100° C. to 170° C., particularly preferably from 120° C. to 150° C., whereas 189° C. corresponds to the boiling point of DMSO.

The solution is further stirred at 90° C. to 189° C., preferably at 100° C. to 170° C., particularly preferably at 120° C. to 150° C. until a suspension is generated, which is characterized by the recurrence of turbidities, wherein preferably the temperature range of the previous dissolution step is maintained, preferably within a range of 10° C., particularly preferably within ±1° C.

The suspension is dried—without stirring—at 90° C. to 189° C., preferably at 100° C. to 170° C., particularly preferably at 120° C. to 150° C., until a finely powdered solid is generated, wherein preferably the temperature range of the previous dissolution step is further maintained, preferably within a range of ±10° C., particularly preferably within ±1° C.

Production Example 1—Embodiment 2

A preferred embodiment for the production of form III comprises the pre-heating of DMSO to a temperature of 90° C. to 189° C., preferably 100° C. to 170° C., particularly preferably 120° C. to 150° C., before any anhydrate form (form I, form II, or a mixture of form I and form II) of 5-amino-2,3-dihydrophthalazine-1,4-dione sodium salt is added to DMSO at a weight ratio of 5-amino-2,3-dihydrophthalazine-1,4-dione sodium salt to DMSO from 1 to 300 up to 1 to 30,000; preferably from 1 to 300 up to 1 to 3,000; particularly preferably from 1 to 300 up to 1 to 350, whereas 189° C. corresponds to the boiling point of DMSO.

The mixture is stirred until complete dissolution—i.e. until apparently there are no more turbidities—at a temperature from 90° C. to 189° C., preferably from 100° C. to 170° C., particularly preferably from 120° C. to 150° C.

The solution is stirred at 90° C. to 189° C., preferably at 100° C. to 170° C., particularly preferably at 120° C. to 150° C. until a suspension is generated, which is characterized by the recurrence of turbidities wherein the temperature range of the previous dissolution step is maintained, preferably within a range of ±10° C., particularly preferably within 1° C.

The suspension is dried—without stirring—at 90° C. to 189° C., preferably at 100° C. to 170° C., particularly preferably at 120° C. to 150° C., until a finely powdered solid is generated, wherein preferably the temperature range of the previous dissolution step is further maintained, preferably within a range of ±10° C., particularly preferably within ±1° C.

Production Example 1—Embodiment 3

In a particularly preferred embodiment of the production example crystalline form III can be produced as follows:

100 mL DMSO are heated in a beaker large enough, preferably in a 200 mL beaker, up to at least 90° C., preferably up to at least 100° C., particularly preferably up to at least 120° C.

Adding 300 mg 5-amino-2,3-dihydrophthalazine-1,4-dione sodium salt anhydrate to DMSO while stirring continuously and maintaining the selected temperature, preferably within a range of ±10° C., particularly preferably within ±1° C.

Stirring the 5-amino-2,3-dihydrophthalazine-1,4-dione sodium salt-DMSO mixture while further maintaining the temperature, preferably within a range of ±10° C., particularly preferably within ±1° C., until complete dissolution, preferably for less than 24 hours, particularly preferably for less than 12 hours.

Stirring the 5-amino-2,3-dihydrophthalazine-1,4-dione sodium salt solution in DMSO while further maintaining the temperature, preferably within a range of ±10° C., particularly preferably within ±1° C., until a suspension is generated, preferably for less than 20 days, particularly preferably for less than 10 days.

Drying the suspension while maintaining the temperature, preferably within a range of +10° C., particularly preferably within ±1° C., however without stirring, until a finely powdered solid is generated, preferably for less than 10 days, particularly preferably for less than 5 days.

Weighing the substance and determining the yield, amounting preferably to more than 200 mg, particularly preferably to almost 300 mg.

Production Example 2—Embodiment 1

A possible production of form III comprises the addition of any anhydrate form of 5-amino-2,3-dihydrophthalazine-1,4-dione sodium salt (form I, form II, or a mixture of form I and form II) to DMSO at a ratio of 5-amino-2,3-dihydrophthalazine-1,4-dione sodium salt to DMSO from 1 to 300 up to 1 to 30,000; preferably from 1 to 300 up to 1 to 3,000; particularly preferably from 1 to 300 up to 1 to 350. The mixture is stirred until complete dissolution—i.e. until apparently there are no more turbidities—at a temperature from 90° C. to 189° C., preferably from 100° C. to 170° C., particularly preferably from 120° C. to 150° C.

The solution is further stirred—while applying a vacuum within the range of $5\times10^{-3}$-$20\times10^{-3}$ mbar, preferably $5\times10^{-3}$-$10\times10^{-3}$ mbar, particularly preferably $8\times10^{-3}$-$10\times10^{-3}$ mbar—at 70° C. to 189° C., preferably at 90° C. to 170° C., particularly preferably at 120° C. to 150° C. until a suspension is generated, which is characterized by the recurrence of turbidities wherein the temperature range of the previous dissolution step is maintained, preferably within a range of ±20° C., particularly preferably within ±5° C.

The suspension is dried under vacuum within the range of $5\times10^{-3}$-$20\times10^{-3}$ mbar, preferably $5\times10^{-3}$-$10\times10^{-3}$ mbar, particularly preferably $8\times10^{3}$-$10\times10^{-3}$ mbar, at 70° C. to 189° C., preferably at 90° C. to 170° C., particularly preferably at 120° C. to 150° C., until a solid is generated, wherein the temperature range of the dissolution step is further maintained, preferably within a range of ±20° C., particularly preferably within ±5° C.

The solid is suspended with 2-propanol and filtered under vacuum utilizing a Büchner funnel. It is rinsed twice with 2-propanol. Subsequently, the finely powdered solid is dried at 50° C. in a drying cabinet to constant mass.

Production example 2 is in particular suitable when larger amounts of starting material are used, e.g. for the production of industrial scale batches.

Production Example 3 Crystalline Form III

To increase the yield of the synthesis a further possible production of form III comprises the addition of 5-amino-2,3-dihydrophthalazine-1,4-dione sodium salt to a DMSO-$H_2O$ mixture (99/1 vol % to 1/99 vol %). Due to the miscibility of DMSO and $H_2O$ and the higher maximum solubility of 5-amino-2,3-dihydrophthalazine-1,4-dione sodium salt in $H_2O$ compared to DMSO a higher proportion of 5-amino-2,3-dihydrophthalazine-1,4-dione sodium salt can be dissolved. Further synthesis is preferentially carried out analogous to the previous production examples.

The solubility of 5-amino-2,3-dihydrophthalazine-1,4-dione sodium salt with regard to the variable proportion of water in the DMSO-$H_2O$ mixture is displayed in FIG. 8. With an increasing proportion of water in the mixture the maximum solubility of 5-amino-2,3-dihydrophthalazine-1,4-dione sodium salt increases continuously. The higher $H_2O$ volume fractions in the DMSO-$H_2O$ mixture are only important for the initial dissolution step. During the subsequent heating step (with regard to a reasonable yield of form III in a preferred temperature range >100° C., see production example 1—embodiments 1 and 2) the $H_2O$ proportion evaporates from the solvent mixture. Without a DMSO proportion with a weight ratio of 5-amino-2,3-dihydrophthalazine-1,4-dione sodium salt to DMSO of at least 1 to 300 (see production example 1—embodiment 1) no 5-amino-2,3-dihydrophthalazine-1,4-dione sodium salt form III is built during the final drying step—or at least no phase-pure form III. The optimum mixing ratio of DMSO to $H_2O$ for the initial dissolution step thus results from the respective industrial production conditions. Generally preferred is a proportion of water in the DMSO-$H_2O$ mixture of 30% to 80%, further preferred of 40% to 70% and mostly preferred of 50% to 60%.

Also production example 3 is suitable when larger amounts of starting material are used and thus for the production of industrial scale batches.

Due to the first step of the production example shown before, namely the selection of a suitable DMSO-$H_2O$ ratio, the maximum solubility of 5-amino-2,3-dihydrophthalazine-1,4-dione sodium salt can be set depending on the intended use. This option is not available in production methods for 5-amino-2,3-dihydrophthalazine-1,4-dione sodium salts described so far. Thus this optional production step for form III itself represents already an advantage over the state of the art.

Possible application examples comprise industrial production of active ingredients and the production of topical applications. For the industrial production of active ingredients following validated GMP requirements the setting of the maximum solubility can be a substantial advantage with regard to the accuracy of the quantity and the phase purity of the desired crystal form. For the production of topical applications this can be an advantage, as herein a maximum solubility in water often is not considered as desirable.

Production Example 4 Crystalline Form II

A possible production of form II comprises initially the production of a pure form of 5-amino-2,3-dihydrophthalazine-1,4-dione sodium salt dihydrate, for instance according to U.S. Pat. No. 6,489,326 B1. Alternatively, any form for 5-amino-2,3-dihydrophthalazine-1,4-dione sodium salt can be dissolved in water while stirring until apparently there are no more turbidities. Herein the ratio of 5-amino-2,3-dihydrophthalazine-1,4-dione sodium salt to water is 1 to 2-50, preferred 1 to 5-50, particularly preferred 1 to 10. Subsequently, 2-propanol is added to the solution and the generated suspension is further stirred. Herein the ratio of the already present solution to propanol is 1 to 2-50, preferred 1 to 4-20, particularly preferred 1 to 8-10. Stirring time is at least 1 hour, preferred at least 2 h, particularly preferred at least 4 h. Subsequently, the suspension is filtered, preferably under vacuum.

The remaining crystalline solid (dihydrate) is then dried at a temperature of 60° C. to 100° C., preferably at 60° C. to 90° C., particularly preferably at 60° C. to 75° C., mostly preferably at 60° C. to 65° C. in a drying cabinet to constant mass.

According to the invention the modifications concerning the methods of production as shown in the production examples and embodiments for form III shall be freely combinable among each other, as long as there are no logical constraints.

Medical Use:

On the basis of the previously described physicochemical and biological characteristics according to the invention form III is suitable—analogous to forms I and II—as active ingredient for use in medicine, in particular for use as anti-inflammatory and immunoregulatory agent, e.g. for the treatment of conditions with excessive immune responses and for the treatment of conditions with an immunodeficient background.

Conditions with excessive immune responses are for instance graft rejections after transplantations; active autoimmune diseases respectively diseases with autoimmune components; in particular active rheumatoid arthritis, relapsing multiple sclerosis, lupoid hepatitis, polyarteritis nodosa, Crohn's disease, colitis ulcerosa, dermatomyositis, Behçet's disease, uveitis in patients with Behçet's disease, idiopathic thrombocytopenic purpura, myasthenia gravis, Lambert-Eaton myasthenic syndrome, polymyositis, psoriasis, psoriasis arthritis, Bekhterev's disease, paroxysmal nocturnal hemoglobinuria, ankylosing spondylitis, autoimmune thyroidites (as e.g. Hashimoto thyroiditis, Ord's thyroiditis or Grave's disease), lupus erythematodes, vitiligo, autoimmune encephalomyelitis, idiopathic optic neuritis, sympathetic ophthalmia, anterior uveitis, retinal degeneration, peripheral ulcerative keratitis, bullous pemphigoid, chronic urticaria, dermatitis herpetiformis Duhring, epidermolysis bullosa acquisita, alopecia areata, autoimmune enteropathy, autoimmune polyendocrine syndromes (as e.g. APECED (autoimmune polyendocrinopathy candidiasis ectodermal dystrophy), Schmidt's syndrome and XPID (X-linked polyendocrinopathy immunodeficiency and diarrhea syndrome)), chronic gastritis, dermatomyositis, diabetes mellitus type 1, diabetes mellitus type 2, Graves' ophthalmopathy, glomerulonephritis, Goodpasture's syndrome, granulomatosis with polyangiitis, Guillain-Barré syndrome, lichen sclerosus, lichen mucosae, IgA pemphigus, microscopic polyangiitis, chronic fatigue syndrome, narcolepsy, PANS (pediatric autoimmune neuropsychiatric syndrome) (as e.g. PANDAS (pediatric autoimmune neuropsychiatric disorders associated with streptococcal infections)), pemphigus foliaceus, pemphigus seborrhoicus, pemphigus vulgaris, polychondritis, polymyalgia rheumatica, rheumatic fever, SAPHO syndrome (synovitis, acne, pustulosis, hyperostosis, osteitis), sarcoidosis, Sjögren's syndrome, scleroderma, stiff-person syndrome, Hennoch-Schönlein purpura, celiac disease, acute disseminated encephalomyelitis, antiphospholipid syndrome, autoimmune cardiomyopathy, autoimmune hemolytic anemia, autoimmune inner ear disease, autoimmune lymphoproliferative syndrome, autoimmune pancreatitis, autoimmune polyendocrine syndrome, autoimmune progesterone dermatitis, Chagas' disease, chronic inflammatory demyelinating polyneuropathy, chronic recurrent multifocal osteomyelitis, COPD (chronic obstructive pulmonary disease), Churg-Strauss syndrome, cold agglutinin disease, adiposis dolorosa, endometriosis, eosinophilic fasciitis, Hashimoto's encephalopathy, acne inversa, interstitial cystitis, Kawasaki disease, Sharp's syndrome, neuromyotonia, opsoclonus myoclonus syndrome, primary biliary cirrhosis, Raynaud's syndrome, restless legs syndrome, transverse myelitis and vasculitis, aplastic anemia, pemphigus, pemphigoid, endogenous uveitis, nephrotic syndrome and atopic dermatitis; as well as septic conditions e.g. induced by infections with Gram-negative or Gram-positive bacteria (e.g. MRSA (methicillin-resistant *Staphylococcus aureus*)) or mycotic pathogens and systemic inflammatory response syndrome (SIRS) induced by other (e.g. immunologic or chemical) factors.

Conditions with immunodeficient background are for instance frequent flues, relapsing respiratory tract infections, relapsing infections of the efferent urinary tract, fatigue, weakness, absent-mindedness of unknown genesis, reconvalescence, chronic viral infections (in particular human immunodeficiency viruses (e.g. HIV-1, HIV-2), hepatitis B, hepatitis C, encephalitis, herpes zoster, herpes simplex, infections of the inner ear, varicella, measles, cytomegaly, Epstein-Barr, adenoviruses, human papilloma viruses and parvoviruses, such as amdoparvoviruses, bocaparvoviruses, dependoparvoviruses, erytrhroparvoviruses and parvovirus spec.), different oncologic diseases (in particular hairy cell leukemia, myeloid leukemia, multiple myeloma, follicular lymphoma, Kaposi's sarcoma, cutaneous T-cell lymphoma, nasopharyngeal carcinoma, carcinoid, renal carcinoma, bladder carcinoma, basal cell carcinomas, metastasizing carcinomas and malignant melanoma), septic granulomatosis, neutropenia, genital warts, keratoses, autoimmune diseases (in particular non-active stages such as relapsing multiple sclerosis between relapses), radiogenic colitis, diverticulitis, allergies (in particular hay fever, polymorphous light eruption, eczema, neurodermatitis), enteritis, colitis, as well as before, during and after chemotherapies and radiation therapies.

Summing up it can be said the form according to the invention is in principle suitable for the treatment of all inflammatory diseases that are associated with a more or less significant increase of pro-inflammatory cytokines, in particular with the increase of IL-6 and TNF alpha. This is—in addition to those already mentioned—also the case for example within the scope of wound healing, e.g. after surgical interventions, for immune processes out of control (as e.g. Keratitis sicca) or for acute and chronic inflammations of unknown etiology (as e.g. tendovaginitis or osteoarthritis).

Pharmaceutical Preparations and Routes of Administration

Pharmaceutical formulations of the active ingredient according to the invention, alone or in combination with adjuvants and standard therapies, can be formulated as liquid and solid and can be administered by any pharmaceutically acceptable way, above all, but nor limiting intravenously, intramuscularly, topically (e.g. conjunctivally as eye drops or transdermally as an ointment or substance-eluting wound pad), parenterally (incl. subcutaneously, intramuscularly, intravenously, intraarterially or intradermally), vaginally, rectally, nasally, or orally, including sublingually and buccally, as well as in form of drug-eluting implants.

Liquid forms can be: e.g. solutions (e.g. for injections and infusions), juices, syrups, drops, teas, suspensions in aqueous or non-aqueous liquids, emulsions, in particular oil-in-water lotions or water-in-oil liquid lotions and sprays.

Solid forms, in particular for oral administration, can be: Tablets, dragées, capsules, pills, fine powders, powders, granulates, or other forms known as suitable to a person skilled in the art, e.g. suppositories.

For topical administrations of the polymorph according to the invention creams, emulsions, lotions, gels, pastes, fine powders, ointments and suspensions are suitable.

Tablets are for example formulated by producing, granulating or dry-pressing a powder mixture, adding a lubricant and a disintegrant and pressing the mixture to a tablet.

Powders are produced by grinding the compound to a suitably fine size and or mixing it with a similarly ground pharmaceutical carrier such as edible carbohydrate such as starch or mannitol. A flavor, preservative, dispersant and colorant can be likewise present.

A granulate is produced by mixing the compound ground for the powder mixture in a suitable manner with a diluent or a base as described before, and, if appropriate, with a binder such as carboxymethyl cellulose, an alginate, gelatin or polyvinyl pyrrolidone, a dissolution retardant such as paraffin, an absorption accelerator such as a quaternary salt and/or an absorbent such as bentonite, kaolin or dicalcium phosphate. The powder mixture can be granulated by wetting it with a binder such as syrup, starch paste, mucilage (e.g. acacia) or solutions of cellulose or polymer materials and pressing it through a sieve.

Alternatively, a powder mixture can be processed by a tableting machine, wherein unevenly formed clumps are generated that can be broken up to granulates. The granulates can be lubricated by adding stearic acid, its salts (stearates), talc or mineral oil in order to avoid a baking at the tableting mold. The lubricated mixture is then pressed to tablets. The compounds according to the invention can also be combined with a free-flowing inert carrier and then be pressed to tablets directly without performing the granulation and dry-press steps.

Capsules are produced by producing a powder mixture as described before and filling it into cast gelatin containers. Glidants and lubricants such as highly dispersible silica, talc, magnesium stearate, calcium stearate or polyethylene glycol as a solid can be added to the powder mixture before filling. A disintegrant or solution enhancer such as agar agar, calcium carbonate or sodium carbonate can be likewise added for improving the availability of the medication after intake of the capsule.

For producing a dosage form as a suppository with the compounds according to the invention waxes with a low melting point as well as a mixture of fatty acid glycerides such as cocoa butter are melted first and then the active ingredient according to the invention is dispersed therein homogeneously under stirring or other mixing methods. The molten homogeneous mixture is then transferred to a suitable mold, let cool down and thus solidified.

The anhydrate form according to the invention can be mixed with all carriers known in the art, for solid dosage forms e.g. with vegetable and animals fats, waxes, paraffins, starch, tragacanth, cellulose derivatives, polyethylene glycol, silicones, bentonites, silica, talc, zinc oxide or mixtures of the aforementioned substances. Thus for an oral administration in form of a tablet or capsule the active ingredient component can be combined e.g. with an oral, non-toxic and pharmaceutically acceptable inert carrier such as ethanol, glycerin, water and the like.

For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethyl glycols, fatty acid esters of sorbitan, or mixtures of the aforementioned substances.

Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth or mixtures of the aforementioned substances.

Excipients may also influence for example the distribution of an active ingredient in different tissues and organs or modify the effect duration or effect velocity of dosage forms, e.g. by accelerating the absorption (e.g. by dimethyl sulfoxide, nicotinic acid, hyaluronidase, taurine), or by retarding the onset of effect, e.g. in depot dosage forms e.g. by polylactide-co-glycolide (PLGA).

In topical application forms the term "penetration enhancers" is used. This comprises e.g. isopropyl myristate, oleic acid, sodium lauryl sulfate and 1,2-propanediol.

Liquid dosage forms comprise solutions, suspensions and emulsions. Examples are isotonic saline solution, Ringer solutions, Ringer lactate solutions, Ringer acetate solutions, water and water/propylene glycol solutions for parenteral injections or the addition of sweeteners and opacifiers for oral solutions, suspensions and emulsions. Liquid dosage forms can also comprise solutions for intranasal administration and eye drops.

Moreover, buffer solutions can be components of pharmaceutical compositions. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid), maleic acid, cacodylate (dimethyl arsenate), carbonic acid, ADA (N-(2-acetamido)imino diacetic acid), PIPES (4-piperazine-bis-ethanesulfonic acid), BIS-TRIS propane (1,3-bis[tris(hydroxymethyl)methylaminol] propane), ethylene diamine, ACES (2-[(amino-2-oxoethyl)amino]ethanesulfonic acid), imidazol, MOPS (3-(N-morphino)-propanesulfonic acid, diethyl malonic acid, TES (2-[tris (hydroxymethyl)methyl]aminoethanesulfonic acid, and HEPES (N-2-hydroxyethylpiperazine-N'-2-ethanesulfonic acid), as well as other buffers with a pKa between 3.8 and 7.7.

Preferred are carbonic acid buffers such as acetate buffer and dicarboxylic acid buffers such as fumarate, tartrate and phthalate as well as tricarboxylic acid buffers such as citrate. A further group of preferred buffers are inorganic buffers such as sulfate, borate, carbonate, oxalate, calcium hydroxide and phosphate buffers. Yet another group of preferred buffers are nitrogen-containing buffers such as imidazol, diethylene diamine and piperazine. Furthermore preferred are sulfonic acid buffers such as TES, HEPES, ACES, PIPES, TAPS ([(2-hydroxy-1,1-bis-(hydroxymethyl)ethyl) amino]-1-propanesulfonic acid), EEPS (4-(2-hydroxyethyl) piperazine-1-propanesulfonic acid), MOPS (4-morpholino-propanesulfonic acid) and BES (N,N-bis-(2-hydroxyethyl)-2-aminoethanesulfonic acid). Another group of preferred buffers are glycine, glycyl-glycine, glycyl-glycyl-glycine, N,N-bis-(2-hydroxyethyl)glycine and N-[2-hydroxy-1,1-bis (hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]-N-methyl arginine, citrulline, ornithine and their derivatives.

Pharmaceutical excipients for use in the respectively desired application form can be for example: Sodium citrate, calcium phosphate, calcium carbonate together with a suitable tablet disintegrant, e.g. for oral administration.

To the disintegrants belong, without being limiting, starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya (Indian tragacanth), locust bean gum, tragacanth, clays such as bentonite, xanthan gum, alginates such as alginic acid and sodium alginate, foaming compositions a.o. Moisture expansion is supported by for example starch, cellulose derivatives, alginates, polysaccharides, dextrans, cross-linked polyvinyl pyrrolidone. The amount of the disintegrant in the composition may vary between 1 and 40% per weight, preferred between 3 and 20% per weight, most preferred between 5 and 10% per weight.

Substances that can produce gas through a reaction with water (sodium hydrogen carbonate, citric and tartric acid) or substances improving the wetting of crystallites as a hydrophilizer and thus support the dissolution e.g. in water (solubilizers, e.g. polyethylene glycol sorbitan fatty acid esters).

Excipients are also substances that can be used as binders such as starch (e.g. from wheat, corn, rice or potato), gelatin, sugars such as glucose, sucrose or beta-lactose, sweeteners (e.g. from corn), natural and synthetic gum such as acacia, tragacanth or ammonium calcium alginate, sodium alginate, polyethylene glycol, polyvinyl pyrrolidone, magnesium aluminium silicate, waxes, cellulose derivatives such as carboxymethyl cellulose, sodium carboxymethyl cellulose, hydroxypropyl carboxymethyl cellulose, or thinners such as sugars (e.g. mannitol).

To the excipients belong for example also lubricants, glidants, flavors or aromas, antioxidants, colorants, preservatives and surface-active substances such as sodium lauryl sulfate or polysorbate 80.

In tablet production, lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more preferred between 0.3 and 3% per weight, most preferred between 0.3 and 1.5% per weight.

To the lubricants used in these dosage forms belong sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol a.o.

Suitable glidants comprise silicon dioxide, magnesium stearate, sodium stearate, starch and talcum. The amount of the glidant in the composition may vary between 0.01 and 10% per weight, preferred between 0.1 and 7% per weight, more preferred between 0.2 and 5% per weight, most preferred between 0.5 and 2% per weight.

Suitable examples for flavors or aromas are essential oils, vitamins and galenic excipients selected from sugars, sugar substitutes, nutritional sweeteners, acidifiers, solubilizers such as water, glycol, glycerin, thickening agents, sweeteners, colorants or preservatives or combinations thereof, also depending from the galenic dosage form.

Suitable aromas and flavors comprise above all essential oils that can be used as aromas, respectively also as flavors. In general, this term refers to volatile extracts from plants or parts of plants with the respective characteristic smell that can be extracted from plants or parts of plants by steam distillation.

As examples can be mentioned: Essential oils, respectively aromatic substances from sage, cloves, chamomile, anise, star anise, thyme, tea tree, peppermint, mint (menthol, cineol), eucalyptus, mango, figs, lavender, chamomile blossoms, pine needles, cypress, oranges, rosewood, plum, currant, cherry, birch leaves, cinnamon, limes, oranges, grapefruit, tangerine, juniper, valerian, lemon balm, lemon grass, palmarosa, cranberry, pomegranate, rosemary, ginger, pineapple, guava, echinacea, ivy leaves, blueberry, kaki, melons etc. or mixtures thereof, such as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

The addition of antioxidants is particularly preferable in topical dosage forms. Suitable examples for antioxidants include sodium metabisulfite, alpha-tocopherol, ascorbic acid, maleic acid, sodium ascorbate, ascorbyl palmitate, butylated hydroxyanisol, butylated hydroxytoluol, fumaric acid or propyl gallate. Preferred antioxidant is sodium metabisulfite.

Colorants are can be for example food colorants. They can be also adsorbed on a suitable adsorption means such as clay or aluminium oxide. The amount of the colorants may vary between 0.01 and 10% per weight of the composition, preferred between 0.05 and 6% per weight, more preferred between 0.1 and 4% per weight, most preferred between 0.1 and 1% per weight.

Suitable colorants are for example curcumin, riboflavin, riboflavin-5'-phosphate, tartrazine, alkanin, quinolione yellow WS, Fast Yellow AB, riboflavin-5'-sodium phosphate, yellow 2G, Sunset yellow FCF, orange GGN, carminic acid, citrus red 2, carmoisine, amaranth, cochineal, Ponceau 4R, Ponceau SX, Ponceau 6R, erythrosine, red 2G, Allura red AC, Indathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminium, silver, gold, pigment rubine, tannin, orcein, ferrous gluconate, and ferrous lactate.

Preservatives for liquid dosage forms can be used on demand. They may be selected from potassium sorbate, methyl ethyl paraben, sodium benzoate and similar substances or mixtures known to a person skilled in the art for this purpose.

Typical examples for preservatives suitable for topical applications are benzyl benzoate, benzoic acid, benzyl alcohol, benzalkonium chloride, N-cetyl-N,N,-trimethylammonium bromide (Cetrimid, Merck), chlorhexidine, chlorbutanol, imidurea, parabens such as methyl-, ethyl-, propyl- or butylparaben, sodium methylparaben, sodium propylparaben, potassium sorbate, sodium benzoate, sodium propionate, phenol, phenoxyethanol, phenylethyl alcohol, phenyl mercuriacetate, phenyl mercuriborate, phenylmercurinitrate, sorbic acid or thiomersal (sodium methylmercurithiosalicylate). Preferred are methylparaben, propylparaben as well as sodium methylparaben and sodium propylparaben.

In topical applications are used surface-active solubilizing agents (solubilizers) such as diethylene glycol monoethyl ester, polyethyl propylene glycol co-polymers, cyclodextrins, glyceryl monostearates such as Solutol HS 15 (Macrogol-15-hydroxystearate from BASF, PEG 660-15 hydroxystearates), sorbitan esters, polyoxyethylene sorbitanic acid esters, polyvinyl alcohol, sodium dodecyl sulfate, (anionic) glyceryl monooleates etc.

Suitable emulsifiers are for example the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters or polyvinyl alcohol. Preferred are glycerin monooleate, stearic acid and phospholipids such as lecithin.

Suitable triglycerides are for example medium-chain and high molecular triglycerides. Medium-chain triglycerides are glycerin esters of fatty acids with only 6-12 carbon atoms such as caprylic/capric acid triglyceride. High molecular triglycerides are glycerin fatty acid esters with long-chained fatty acids. They are for example, triglyceride mixtures produced from several naturally occurring fats. Preferred are medium-chain triglycerides, in particular caprylic/capric acid triglyceride.

Suitable pH-regulators for topical dosage forms are e.g. sodium hydroxide, hydrochloric acid, buffer substances such as sodium dihydrogen phosphate or disodium hydrogenphosphate.

Cream preparations may also contain other excipients and additives, such as fatiquors, solvents, consistency enhancers or hydrotropes for improving the flow characteristics. Herein single as well as several substances from the same group of additives or excipients may be present in the mixture.

Suitable fatiquors are e.g. oleic acid decylester, hydrated castor oil, light mineral oil, mineral oil, polyethylene glycol, sodium laurylsulfate.

Suitable solvents are corn oil, cottonseed oil, peanut oil, sesame oil, soybean oil, ethyl oleate, glycerin, isopropyl myristate, isopropyl palmitate, polyethylene glycol or polypropylene glycol.

Suitable consistency enhancers are e.g. cetyl alcohol, cetyl ester wax, hydrated castor oil, microcrystalline waxes, non-ionic emulsifier waxes, beeswax, paraffin or stearyl alcohol.

Suitable hydrotropes are alcohols such as ethanol, isopropyl alcohol or polyols such as glycerin.

Application Examples

Possible applications are for example, without being limiting, the following:

Parenteral applications are for example suitable for acute and peracute conditions with hospitalization such as septic conditions, or in the course of planned surgical interventions. Suitable active ingredient dosages of Form III according to the invention range from 1 µg to 100 mg/kg body weight, preferred from 50 µg to 10 mg/kg body weight, particularly preferred from 100 µg to 5 mg/kg body weight. It can be administered once or twice daily or via permanent infusion, wherein the total daily dose preferably is max. 100 mg/kg body weight, particularly preferred max. 50 mg/kg body weight. For surgical interventions it is recommended to start the dosing at least 12 h, preferred 24 h, particularly preferred at least 48 h before the actual intervention. The duration of the treatment depends on the patient's condition and the nature of the disease. The treatment should be continued at least to absence of symptoms, preferred for at least 2 days more after absence of symptoms, particularly preferred at least 5 days more after absence of symptoms.

Peroral applications such as tablets or capsules are for example suitable for acute, subacute, chronic or relapsing conditions such as rheumatoid arthritis. Suitable active ingredient dosages for Form III according to the invention range from 1 µg to 100 mg/kg body weight, preferred from 50 µg to 10 mg/kg body weight, particularly preferred from 100 µg to 5 mg/kg body weight. The intake may be once or twice daily, wherein the total daily dose preferably is max. 100 mg/kg body weight, particularly preferred max. 50 mg/kg body weight. The interval between two applications should be preferably min. one hour, particularly preferred min. 2 hours. The duration of the treatment depends on the patient's condition and the nature of the disease. The treatment should be continued at least to absence of symptoms, preferred for at least 6 days more after absence of symptoms, particularly preferred at least 14 days more after absence of symptoms.

Topical applications such as eye drops or ointments are for example suitable in form of eye drops for the treatment of inflammatory diseases of the eye, and for example in form of an ointment or cream for the treatment of wounds or inflammatory skin diseases. In the pharmaceutical composition suitable percentages of the active ingredient for Form III according to the invention range from 0.05 to 20%, preferred from 0.1 to 10%, particularly preferred from 0.2 to 5%. The application may be once or twice daily, wherein the interval between two applications should be preferably min. one hour, particularly preferred min. 2 hours. The duration of the treatment depends on the patient's condition and the nature of the disease. The treatment should be continued at least to absence of symptoms, preferred for at least 3 days more after absence of symptoms, particularly preferred at least 10 days more after absence of symptoms.

Inventive crystalline Form III of 5-amino-2,3-dihydrophthalazine-1,4-dione sodium salt can also be used in combination with at least one further known active ingredient and/or standard therapy.

These active ingredients for combinations can be selected from the group comprising steroidal and non-steroidal anti-inflammatory agents, immunomodulators, immunosuppressive agents, antibiotics, anti-infective agents, antiviral agents, antimycotics, analgesics, local anesthetics, anticoagulants, thrombocyte aggregation inhibitors, muscle relaxants, tonic agents and anabolic agents. Such a combination of active ingredients can be used for prophylactic and/or therapeutic purposes in a person in need of such an administration.

Suitable examples for steroidal anti-inflammatory agents comprise corticosteroids, glucocorticoids, cortisone, cortisone acetate, hydrocortisone, hydrocortisone acetate, dexamethasone, betamethasone, prednisone, prednisolone, methylprednisolone, deltasone, triamcinolone, tixocortol pivalate, mometasone, amcinonide, budesonide, desonide, fluociconide, fluocinolone, halcinonide, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, flunisolide, fluticasone furoate, fluticasone propionate, triamcinolone acetonide, beclomethasone dipropionate.

Suitable examples for non-steroidal anti-inflammatory drugs (NSAIDs) comprise acetylsalicylic acid, salicylic acid and salicylates, paracetamol (acetaminophen), salsalate, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celexoxib, rofecoxib, valdecoxib, parecoxib, lumiracoxib, etoricoxib, firocoxib, nimesulide, clonixin, licofelone, H-harpagide, flunixin, tiaprofenic acid.

Suitable examples for immunomodulatory agents (IMIDs) comprise thalidomide, lenalidomide, pomalidomide and apremilast.

Suitable examples for antiviral agents comprise ancriviroc, aplaviroc, cenicriviroc, enfuvirtide, maraviroc, vicriviroc, amantadine, rimantadine, pleconaril, idoxuridine, aciclovir, brivudine, famciclovir, penciclovir, sorivudine, valaciclovir, cidofovir, ganciclovir, valganciclovir, sofosbusvir, foscarnet, ribavirine, taribavirine, filibuvir, nesbuvir, tegobuvir, fosdevirine, favipiravir, merimepodib, asunaprevir, balapiravir, boceprevir, ciluprevir, danoprevir, daclatasvir, narlaprevir, telaprevir, simeprevir, vaniprevir, rupintrivir, fomivirsen, amenamevir, alisporivir, bevirimate, letermovir, laninamivir, oseltamivir, peramivir, zanamivir.

Suitable examples for immunostimulatory agents comprise interferons (α-, β-, γ-, τ-interferon), interleukins, CSF, PDGF, EGF, IGF, THF, levamisol, dimepranol, inosine.

Suitable examples for immunosuppressive agents comprise the group of glucocorticoids, as described before; cytostatic agents such as alkylating agents (such as cyclophosphamide), Antimetabolites such as methotrexate, azathioprine, mercaptopurine, fluorouracil, leflunomide, protein synthesis inhibitors and certain antibiotics such as dactinomycine, anthracyclines, mitomycine C, bleomycine and mithramycine, intercalating agents such as mitoxantrone; antibodies such as muromonab-CD3, rituximab, ustekinumab, alemtuzumab, natalizumab, basiliximab and daclizumab; agents acting on immunophilins such as cyclosporine, tacrolimus and sirolimus; and non-classified immunosuppressive agents such as β-interferon, γ-interferon, opioids, TNF-binding proteins such as infliximab, etanercept, adalimumab; or curcumin, catechins, mycophenolic acid, fingolimod, myriocin and fumaric acid dimethyl ester.

Suitable examples for antibiotics comprise imipenem, meropenem, ertapenem, cephalosporins, aztreonam, penicillines such as penicillin G and penicillin V, piperacillin, mezlocillin, ampicillin, amoxicillin, flucloxacillin, methicillin, oxacillin, clavulanic acid, sulbactam, tazobactam, sultamicillin, fosfomycine, teicoplanin, vancomycin, bacitracin, colistine, gramicidin, polymyxin B, tyrothricin, teixobactin, fosmidomycin, amikacin, gentamicin, kanamycin, neomycin, netilmicin, streptomycin, tobramycin, chloramphenicol, fusidinic acid, cethromycin, narbomycin, telithromycin, clindamycin, lincomycin, daptomycin, dalfopristin, quinupristin, azithromycin, clarithromycin, erythromycin, roxithromycin, linezolid, doxycycline, minocycline, tetracycline, oxytetracycline, tigecycline, norfloxacin, enoxacin, ciprofloxacin, ofloxacin, levofloxacin, moxifloxacin, metronidazole, tinidazole, aminocumarine, sulfadiazine, sulfadoxine, sulfamethoxazol, sulfasalazine, pyrimethamine, trimethoprim, and rifampicin.

Anti-infective agents is a generic term for compounds used in the treatment of bacterial, viral, fungal, protozoal and worm infections and comprises antibiotics, antiviral agents, antimycotics, antiprotozoal agents and anthelmintics.

Suitable examples for muscle relaxants comprise tercuronium, 1-ethylcarbamoyl-3-(3-trifluoromethylphenyl)pyrrolidine, metaxalone, methocarbamol, meprobamate, baclofen, carisoprodol, chlorzoxanzone, cyclobenzaprine, dantrolene, diazepam, orphenadrine, quinine, rocuronium, succinylcholine, decamethonium, pancuronium, veruronium, rapacuronium, dacuronium, duador, malouetine, dipyrandium, pipercuronium, chandonium, HS-342, atracurium, mivacurium, doxacurium, d-tubocurarine, dimethyltubocurarine, gallamine, alcuronium, anatruxonium, diadonium, fazadinium, tropeinium, cisatrucurium.

Suitable examples for antimycotics comprise abafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, amorolfine, butenafine, nafitifine, terbinafine, anidulafungin, caspofungin, micafungin, benzoic acid, ciclopirox, flucytosine, griseofulvin, haloprogin, tolnaftate, undecylenic acid, crystal violet, Peru balm.

Suitable examples for antiprotozoal agents comprise metronidazole, tinidazole, ornidazole, atovaquone, clioquinole, chlorquinaldole, emetine, pentamidine isethionate, eflornithine, nitrofural, halofuginone, miltefosine, chloroquine, hydroxychloroquine, mepacrine, primaquine, amodiaquine, pamaquine, piperaquine, proguanil, cyclohunail embonate, quinine, mefloquine, pyrimethamine, artmether, artemisinine, artesunate, dihydroartemisinine, halofantrine, lumefantrine, sulfadoxine.

Suitable examples for anthelmintics comprise mebendazole, praziquantel, albendazole, diethylcarbamazine, flubendazole, ivermectin, levamisole, metrifonate, niclosamide, oxyclozanide, oxamniquine, oxantel, piperazine, pyrantel, pyrantel pamoate, monopantel, derquantel, pelletierine sulfate, pyrvinium, thiabendazole, fenbendazole, triclabendazole, abamectin, suramine, emodepside, pyrvinium embonate, aminoacetonitrile.

Suitable examples for local anesthetics comprise lidocaine, lignocaine, menthol, articaine, bupivacaine, ropivacaine, benzocaine, chloroprocaine, cocaine, cyclomethycaine, dimethocaine, larocaine, piperocaine, propoxycaine, procaine, novocaine, proparacaine, tetracaine, amethocaine, cinchocaine, dibucaine, etidocaine, levobupivacaine, meplavacaine, prilocaine, trimecaine, saxitoxin, neosaxitoxin, tetrodotoxin, eugenol.

Suitable examples for analgesics comprise the NSAIDs listed above; opioid analgesics such as morphine, fentanyl, methadone, oxycodone, carfetanyl, dihydroetorphine, ohmefentanyl, etorphine, sufentanil, remifentanil, alfentanil, buprenorphine, hydromorphone, levomethadone, hydrocodone, pintramide, nalbuphine, tapentadol, pentazocine, dihydrocodeine, codeine, pethidine, tramadol, tilidine, meptazinol, naloxone, naltrexone, diprenorphine, loperamide, apomorphine; epibatidine; scopolamine; ziconitide; cannabinoids such as tetrahydrocannabinol, cannabidiol, marinol; flupirtine; ketamine and the local anesthetics listed above.

Suitable examples for anticoagulants comprise heparins, coumarins such as phenprocoumon (Marcumar) and warfarin, apixaban, rivaroxaban, edoxaban, dabigatran, ximelagatran, hirudin, lepirudine, bivalirudine, citrate, EDTA, fondaparinux, argatroban, otamixaban.

Suitable examples for thrombocyte aggregation inhibitors comprise abciximab, acetylsalicylic acid, dipyridamole, clopidogrel, eptifibatide, ilomedine, prostacyclin, prasugrel, ticagrelor, ticlopidine, tirofiban.

Tonic agents is a generic term for active ingredients that strengthen the body, augment the tonus or restore its physiological functions. They may be of herbal or animal origin.

Anabolic agents may support the anabolic metabolism and a strengthening of the cellular collagen scaffold. However, a wide abuse of these substances for doping in sports and bodybuilding is known. Hence, a combination with the crystalline Form III of 5-amino-2,3-dihydrophthalazine-1,4-dione sodium salt is only recommended insofar this is covered by the respective national legislations.

Standard therapies for the aforementioned active ingredients can be easily found in the art by a skilled person. It is preferred that the respective application forms and doses of the aforementioned combinations of active ingredients follow the already established standard therapies for the combinational active ingredient besides the inventive crystalline Form III of 5-amino-2,3-dihydrophthalazine-1,4-dione sodium salt.

Abbreviations:

| | |
|---|---|
| vol % | percent by volume |
| fig. | figure |
| ca. | circa |
| $cm^{-1}$ | wave-number |
| $cm^3$ | cubic centimeter |
| DMSO | dimethyl sulfoxide |
| FT-IR | Fourier-Transformation Infrared |
| g | gram |
| wt % | percent by weight (mass fraction) |
| GMP | Good Manufacturing Practice |
| GPP | Good Pharmacy Practice |
| h | hour |
| $H_2O$ | water |
| IL | interleukin |
| kg | kilogram |
| l | liter |
| LPS | lipopolysaccharides |
| $m^3$ | cubic meter |
| mbar | millibar |
| mg | milligram |
| mL | milliliter |
| mmol | millimol |
| mol | mol |
| nm | nanometer |
| pg | pikogram |
| PMA | phorbol 12-myristate 13-acetate |
| SEM | scanning electron microscope |
| RT | room temperature |
| s | standard deviation |
| TNF | tumor necrosis factor |
| a.o. | amongst others |
| fd | fully demineralized |
| cf. | confer |
| XRPD | X-ray powder diffractogram |
| e.g. | exempli gratia |

The invention claimed is:

1. A crystalline form III of 5-amino-2,3-dihydrophthalazine-1,4-dione sodium salt anhydrate, characterized by crystallography values determined by means of X-ray powder diagrams:

d values: 13.131; 7.987; 7.186; 6.566; 6.512; 5.372; 3.994; 3.662; 3.406; 3.288; 3.283; 3.222; 3.215; 3.127; 2.889 and 2-theta values: 6.73; 11.07; 12.31; 13.48; 13.59; 16.49; 22.24; 24.29; 26.14; 27.10; 27.14; 27.67; 27.72; 28.52; 30.93.

2. The crystalline form according to claim 1, characterized by a content of water of crystallization ≤0.4%.

* * * * *